(12) United States Patent
Wolf et al.

(10) Patent No.: US 9,085,511 B2
(45) Date of Patent: Jul. 21, 2015

(54) ATROPISOMERIC 1,8-BISPHENOLNAPTHALENES AND THEIR USE IN ENANTIOSELECTIVE RECOGNITION AND ASYMMETRIC SYNTHESIS

(75) Inventors: Christian Wolf, Arlington, VA (US);
Marwan Ghosn, Alekabar (SA)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 14/009,572

(22) PCT Filed: Apr. 3, 2012

(86) PCT No.: PCT/US2012/031994
§ 371 (c)(1),
(2), (4) Date: Jan. 17, 2014

(87) PCT Pub. No.: WO2012/138654
PCT Pub. Date: Oct. 11, 2012

(65) Prior Publication Data
US 2014/0128637 A1 May 8, 2014

Related U.S. Application Data

(60) Provisional application No. 61/471,450, filed on Apr. 4, 2011.

(51) Int. Cl.
*C07C 249/00* (2006.01)
*C07C 39/21* (2006.01)
(Continued)

(52) U.S. Cl.
CPC .............. *C07C 249/00* (2013.01); *C07C 39/15* (2013.01); *C07C 39/21* (2013.01); *C07C 47/57* (2013.01);
(Continued)

(58) Field of Classification Search
None
See application file for complete search history.

(56) References Cited

U.S. PATENT DOCUMENTS 7,888,509 B2    2/2011  Wolf et al.

OTHER PUBLICATIONS

Database CAPLUS on STN, Acc. No. 2002:462935, Kang et al., Journal of the American Chemical Society (2002), 124(28), pp. 8275-8279 (abstract).*

(Continued)

*Primary Examiner* — Brian J Davis
(74) *Attorney, Agent, or Firm* — Matthew K. Ryan; Blaine M. Hackman; Frommer Lawrence & Haug LLP

(57) ABSTRACT

This invention related to atropisomeric 1,8-bisphenolnaphthalenes and derivatives thereof of the general formula (I):

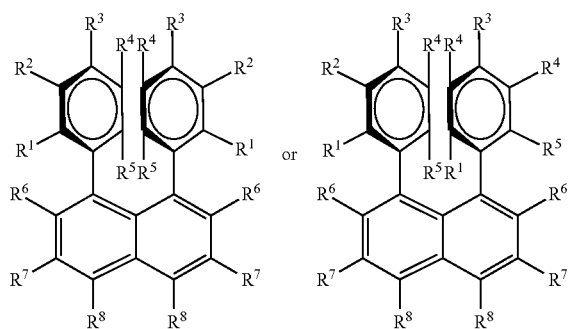

which are useful in resolution of enantiomers, enantioselective recognition and asymmetric synthesis.

9 Claims, 30 Drawing Sheets

(51) Int. Cl.
*C07C 47/57* (2006.01)
*C07C 39/15* (2006.01)
*C07C 209/88* (2006.01)

(52) U.S. Cl.
CPC ........... C07C 209/88 (2013.01); *C07B 2200/07* (2013.01); *C07C 2101/14* (2013.01); *C07C 2102/42* (2013.01)

(56) References Cited

OTHER PUBLICATIONS

Database CAPLUS on STN, Acc. No. 2000:597924, Iovine et al., Journal of the American Chemical Society (2000), 122(36), pp. 8717-8727 (abstract).*

Ghosn, Marwan W. et al., "Enantioselective recognition of amines with an atropisomeric 1,8-bisphenolnaphthalene", Tetrahedron 2011, vol. 67, 6799-6803. (Jul. 6, 2011).

Ghosn, Marwan W. et al., "Synthesis, Conformational Stability, and Asymmetric Transformation of Atropisomeric 1,8-Bisphenolnaphthalenes", J. Org. Chem. 2011, vol. 76, 3888-3897. (Apr. 8, 2011).

Iovine, Peter M. et al., "Syntheses and 1H NMR Spectroscopy of Rigid, Cofacially Aligned, Porphyrin-Bridge-Quinone Systems in Which the Interplanar Separations between the Porphyrin. Aromatic Bridge, and Quinone Are Less than the Sum of Their Respective van der Weals Radii", J. Am. Chem. Soc. 2000, vol. 122, 8717-8727.

Pieters, Gregory et al., "Synthesis and Molecular Structure of Symmetrical 1,8-Diarylnaphthalenes", Eur. J. Org. Chem. 2010, 5800-5806. (Sep. 1, 2010).

Steele, Melanie et al., "Attempts to find a solution to the problem of atropisomer interconversion in 1,8-diarylnaphthalenes and 5,6-diarylacenaphthens", J. Chern. Soc Perkin. Trans 1, 2001, 588-598.

Bringmann, Gerhard et al., "Enantioselective addition of diethylzinc to aldehydes using novel axially chiral 2-aminomethyl-I-(2'-hydroxyphenyl)naphthalene catalysts", Tetrahedron: Asymmetry 1998, vol. 9, 667-679.

Search Report issued in application PCT/US2012/031994 dated Nov. 30, 2012.

* cited by examiner

ATROPISOMERIC 1,8-BISPHENOLNAPTHALENES AND THEIR USE IN ENANTIOSELECTIVE RECOGNITION AND ASYMMETRIC SYNTHESIS

STATEMENT OF PRIORITY

This application claims priority to U.S. Provisional Appl. No. 61/471,450, filed Apr. 4, 2011, the disclosure of which is hereby incorporated by reference.

STATEMENT OF GOVERNMENT INTEREST

This invention was made in part with government support under grant number CHE-0910604, awarded by the National Science Foundation. The government has certain rights to this invention.

INCORPORATION BY REFERENCE

The documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated by reference, and may be employed in the practice of the invention.

FIELD OF THE INVENTION

This invention related to atropisomeric 1,8-bisphenolnaphthalenes and derivatives thereof of the general formula (I):

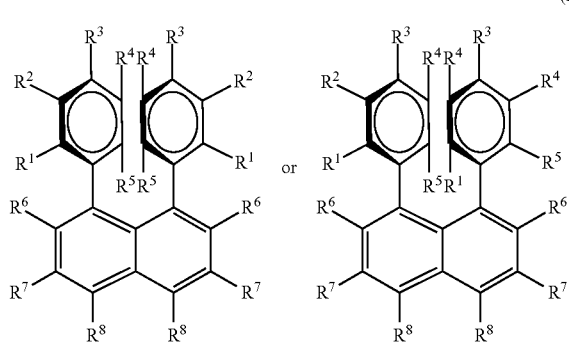

which are useful in resolution of enanatiomers, enantioselective recognition and asymmetric synthesis.

BACKGROUND OF THE INVENTION

The intriguing structure and dynamic stereochemistry of axially chiral compounds has fueled their use in asymmetric synthesis, chiral recognition, the design of microscopic devices such as molecular motors and switches, drug discovery and other areas. (Wolf, C. (Ed.) Dynamic Stereochemistry of Chiral Compounds, RSC, Cambridge, 2008.) Undoubtedly, the exceptional diversity and the unique stereochemical, electronic, and photochemical properties of both conformationally stable and rapidly racemizing axially chiral biaryls and polyaryls have led to a wide variety of applications. (See e.g., Qiao, X.; Padula, M. A.; Ho, D. M.; Vogelaar, N. J.; Schutt, C. E.; Pascal Jr., R. A. *J. Am. Chem. Soc.* 1996, 118, 741-745.) It is therefore not surprising that structural analysis along with the study of enantiomerization and diastereomerization processes of mono- and disubstituted naphthalenes have received significant attention. (See e.g., Casarini, D.; Lunazzi, L.; Macciantelli, D. *Tetrahedron Lett.* 1984, 25, 3641-3642). Alkyl, (See, e.g., Fields, D. L.; Regan, T. H. *J. Org. Chem.* 1971, 36, 2986-2990.) aryl (See, e.g. House, H. O.; Magin, R. W.; Thompson, H. W. *J. Org. Chem.* 1963, 28, 2403-2406.) and heteroaryl (See, e.g. Zoltewicz, J. A.; Maier, N. M.; Fabian, W. M. F. *Tetrahedron* 1996, 52, 8703-8706.) groups have been introduced into the naphthalene framework to study the energy barrier to rotation about the naphthyl-alkyl or naphthyl-aryl bond and intramolecular interactions between proximate alkyl and aryl groups.

In particular, the incorporation of two phenol rings into a rigid $C_2$-symmetric scaffold that is reminiscent of the successful BINOL motif has been of general interest due to potential applications in asymmetric catalysis and enantioselective sensing for a long time. (See e.g., Pritchard, R. G.; Steele, M.; Watkinson, M.; Whiting, A. *Tetrahedron Lett.* 2000, 41, 6915-6918.)

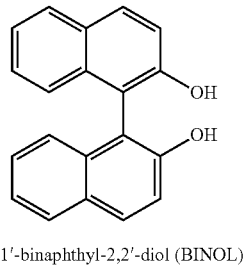

1,1'-binaphthyl-2,2'-diol (BINOL)

Although the synthesis of BINOL was first reported in 1873 it took another 100 years until this prime example of a $C_2$-symmetric bidentate atropisomer gained considerable attention. (See von Richter, V. *Chem. Ber.* 1873, 6, 1249-1260.) Since the mid 1970s, BINOL and its derivatives have found extensive use in asymmetric reactions, molecular recognition studies and other applications. (See e.g., Pu, L. *Chem. Rev.* 1998, 98, 2405-2494.) The intriguing structure of BINOL and its success as chiral ligand and reagent in asymmetric synthesis has propelled the development of countless analogues that vary in stereoelectronic properties and bite angle. For many years, the synthesis of axially chiral 1,8-bisphenolnaphthalenes has been pursued due to the apparent structural analogy to BINOL and the associated promise in asymmetric catalysis and other areas.

Other attempts to synthesize derivatives of BINOL include the applicants previous work described in U.S. Pat. No. 7,888,509 which included general references to aryl and heteroaryl derivatives of naphthalene and specific examples directed to diacridine derivatives of naphthalene (core structure of diacridine derivative shown below).

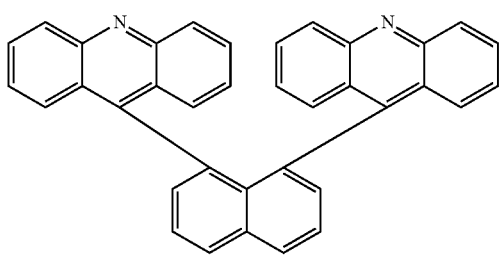 [SMILES: c1cc(-c2c3ccccc3nc3ccccc23)c2c(-c3c4ccccc4nc4ccccc34)cccc2c1]

However, the incorporation of sufficient steric bulk into the chiral 1,8-bisphenolnaphthalene framework to halt rotation about the aryl-aryl axes and concomitant racemization has proven difficult. (See e.g., Pritchard, R. G.; Steele, M.; Watkinson, M.; Whiting, A. *Tetrahedron Lett.* 2000.) Accordingly, few stereodynamic 1,8-bisphenolnaphthalenes such as 1,8-bis(3'-formyl-4'-hydroxyphenyl)naphthalene, 1 have been reported to date and used in racemic form. (See e.g., Watkinson, M.; Whiting, A.; McAuliffe, C. A. *J. Chem. Soc., Chem. Commun.* 1994, 2141.)

Therefore, a need still exists in the art for 1,8-bisphenolnaphthalene derivatives which are isolatable and suitable for use in resolution of enantiomers, enantioselective recognition and asymmetric synthesis.

SUMMARY OF THE INVENTION

The applicants have addressed the need in the art for 1,8-bisphenolnaphthalene derivatives which are isolatable and suitable for use in enantioselective recognition and asymmetric synthesis by providing 1,8-bisphenolnaphthalene compounds with ortho and meta substitution on the phenolic ring relative to its bonding with napthalene.

One aspect of the invention relates to atropisomeric 1,8-bisphenolnaphthalene compounds of formula (I):

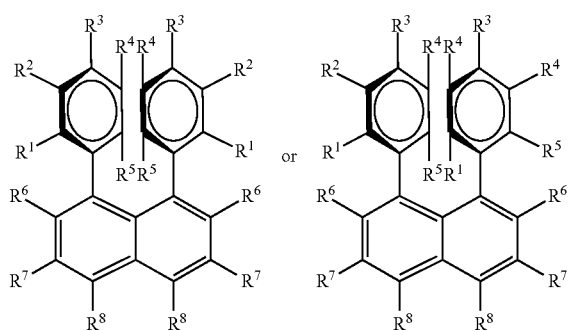

wherein $R^1$, $R^2$, $R^3$, $R^4$, $R^5$, $R^6$, $R^7$ and $R^8$ are described herein.

Another aspect of the invention relates to the process of making the atropisomeric 1,8-bisphenolnaphthalene compounds of formula (I).

Another aspect of the invention relates to the process of converting one conformer of the atropisomeric 1,8-bisphenolnaphthalene compounds of formula (I) into another conformeric form and optionally, to isolate the conformer.

Another aspect of the invention relates to a method of providing enantiomeric recognition between stereoisomers of a compound which comprising of adding an atropisomeric 1,8-bisphenolnaphthalene compounds of formula (I).

Another aspect of the invention relates to the process of separating enantiomers from a racemic mixture of atropisomeric 1,8-bisphenolnaphthalene compounds of formula (I).

Another aspect of the invention relates to a method of conducting asymmetric synthesis of a compound which comprising of adding an atropisomeric 1,8-bisphenolnaphthalene compounds of formula (I).

These aspects of the invention and other aspects of the invention are disclosed or are apparent from and encompassed by, the Detailed Description which follows below.

For the purposes of this application the following terms have the meanings defined below:

"atropisomer"—stereoisomers resulting from hindered rotation about single bonds where the steric strain barrier to rotation is high enough to allow for the isolation of conformers.

"de"—diastereomeric excess

"hydroxy protecting group"—refers to known —OH protecting groups to those of skill in the art which includes, but is not limited to those described in *Protective Groups in Organic Synthesis (Fourth Edition)*, Theodora W. Greene and Peter G. M. Wuts, Wiley-Interscience (October 2006).

For the compound of formula (I) and all subsequent formulae, terms for chemical radicals are used are defined as follows.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc.; this applies correspondingly to hydrocarbon radicals in composite meanings, such as hydrocarbonoxy radicals or other hydrocarbon radicals attached via heteroatom groups.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

By way of example, the expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, for example "$(C_1-C_6)$-alkyl" correspondingly also include straight-chain or branched alkyl radicals having a larger number of carbon atoms, i.e., according to the example, also the alkyl radicals having 5 and 6 carbon atoms.

Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl.

Alkynyl also includes, in particular, straight-chain or branched hydrocarbon radicals having more than one triple bond or else having one or more triple bonds and one or more double bonds, for example 1,3-butatrienyl or 3-penten-1-yn-1-yl (pent-3-en-1-yn-1-yl).

A carbocyclic ring is any form of a closed ring of carbon atoms and can include alicyclic or aromatic structures. Examples of such structures include, but are not limited to ($C_3$-$C_9$)-cycloalkyl which is a carbocyclic saturated ring system having 3-9 ring carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene. Further examples include, but are not limited to ($C_5$-$C_9$)-cycloalkenyl which is a carbocyclic, nonaromatic, partially unsaturated ring system having 5-9 ring carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of ($C_1$-$C_{10}$)-alkylidene, is the radical of a straight-chain or branched alkane which is bonded via a double bond, the position of the binding site not being fixed. In the case of a branched alkane, of course, only positions at which two hydrogen atoms may be replaced by the double bond are possible; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are, respectively, alkyl, alkenyl and alkynyl substituted partly or fully by identical or different halogen atoms, preferably from the group of fluorine, chlorine and bromine, in particular from the group of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

Aryl is a mono-, bi- or polycyclic carbocyclic aromatic system, for example phenyl, naphthyl, tetrahydronaphthyl, indenyl, indanyl, pentalenyl, fluorenyl and the like, preferably phenyl.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, e.g. by a heteroatom from the group consisting of N, O, S, P, B, Si, Se), which is saturated, unsaturated or heteroaromatic and may be unsubstituted or substituted, where the point of attachment is located at a ring atom.

If the heterocyclyl radical or the heterocyclic ring is optionally substituted, it can be fused to other carbocyclic or heterocyclic rings.

Optionally substituted heterocyclyl also includes polycyclic systems, such as, for example, 8-aza-bicyclo[3.2.1]octanyl or 1-aza-bicyclo[2.2.1]heptyl.

Optionally substituted heterocyclyl also includes spirocyclic systems, such as, for example, 1-oxa-5-aza-spiro[2.3]hexyl.

Heteroaryl means, from among the systems defined above under "heterocyclyl", in each case a heteroaromatic compound, i.e. a fully unsaturated aromatic heterocyclic compound.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals selected from the group of halogen, alkoxy, alkylthio, $SF_5$, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as the substituted alkyl, alkenyl, alkynyl, cycloalkyl, aryl, phenyl, benzyl, heterocyclyl and heteroaryl radicals mentioned, substituents include, in addition to the saturated hydrocarbon radicals mentioned such as alkyl, alkoxy, alkylthio, alkoxycarbonyl, haloalkyl, cycloalkyl or cycloalkyloxy, corresponding unsaturated aliphatic and aromatic radicals, such as optionally substituted alkenyl, alkynyl, alkenyloxy, alkynyloxy, phenyl and phenoxy. In the case of substituted cyclic radicals having aliphatic moieties in the ring, cyclic systems with those substituents which are bonded on the ring by a double bond are also included, for example substituted by an alkylidene group such as methylidene or ethylidene.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids.

The "yl position" of a radical denotes the carbon atom having the free bond. Compounds of the formula (I) according to the invention and compounds of the formula (I) used according to the invention (and, if appropriate, salts thereof) are in short also referred to as "compounds (I)".

In addition, for the purposes of this application compounds of the invention also include all stereoisomers and racemic mixtures thereof. The possible stereoisomers defined by their specific three-dimensional shape, such as enantiomers, diastereomers, Z- and E-isomers, are all encompassed by the formula (I) and can, in the preferred enantioselective procedure, be prepared selectively when optically active materials are used. The application also includes all tautomeric forms, pharmaceutically acceptable salts and crystalline forms including polymorphic forms.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
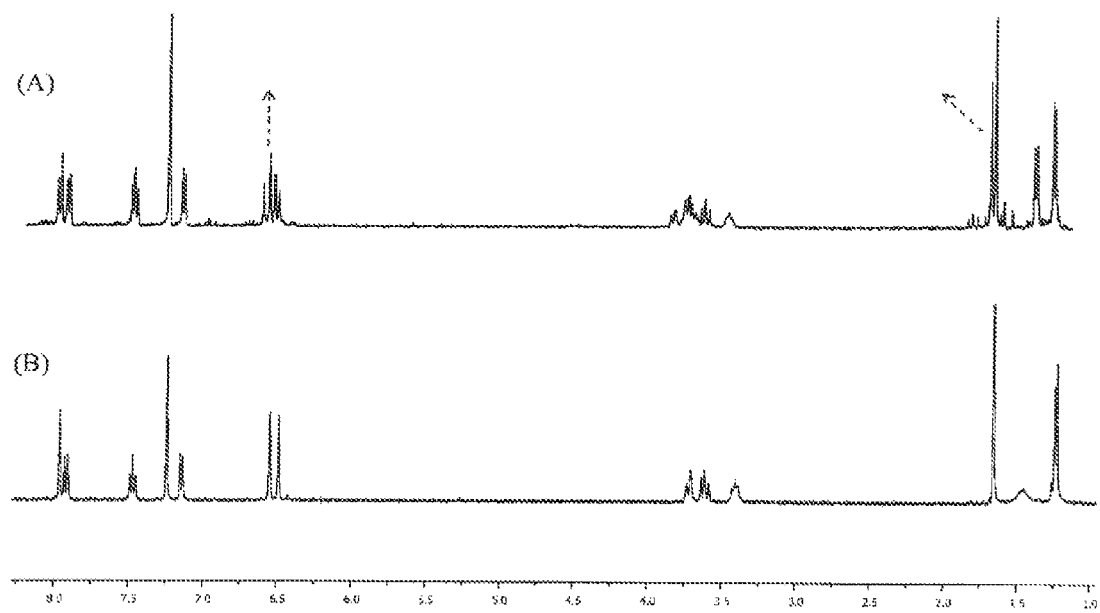
FIG. 1 depicts $^1$H NMR spectra of diimine diastereomers obtained from racemic 5 and (R)-2-amino-1-propanol and quantitative conversion towards (P,P,R,R)-9. (A) 60° C., 0 h, (B) 60.0° C., 14 h. * corresponds to (M,M,R,R)-9, ‡ corresponds to (P,P,R,R)-9.

One aspect of the invention relates to atropisomeric 1,8-bisphenolnaphthalene compounds of formula (I).

One embodiment of this aspect of the invention is the atropisomeric 1,8-bisphenolnaphthalene compounds of formula (I):

(I)

wherein
$R^1$ and $R^5$ independently selected from the group consisting of hydrogen, alkyl, alkenyl, alkynyl, cycloalkyl, aryl, benzyl, heterocyclyl, heteroaryl, chloro, bromo, iodo, acyl, amino, amido, azido, cyano, formyl, carbamoyl, —SF$_5$, nitro, —OR', —NR"R''', —SR'''', P(O)(OR$^A$)$_2$, —P(OR$^A$)$_2$, and P(RB)$_2$,
wherein
R' is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical, P(O)(OR$^A$)$_2$, —P(OR$^A$)$_2$, and P(R$^B$)$_2$; or OR' is an optionally substituted saturated or unsaturated, non-aromatic or aromatic heterocyclic radical;

R" and R'" are each independently of one another H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or NR"R'" is an optionally substituted saturated or unsaturated, nonaromatic or aromatic heterocyclic radical;

R"" are each independently of one another H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or SR" is an optionally saturated or unsaturated, nonaromatic or aromatic heterocyclic radical;

$R^A$ is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;

$R^B$ is H, halogen, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;

wherein at least one of $R^1$ and $R^5$ on each phenyl ring is not hydrogen;

$R^2$, $R^3$, $R^4$, $R^6$, $R^7$ and $R^8$ are independently selected from the group consisting of hydrogen, alkyl, alkenyl, alkynyl, cycloalkyl, aryl, benzyl, heteroalkyl, heterocyclyl, heterocycloalkyl, heteroaryl, halogen, acyl, amino, amido, azido, alkyliminyl (—C=NH-alkyl), carboxy, cyano, formyl, carbamoyl, —$SF_5$, nitro, OR', NR"R'", SR"", P(O)(OR$^A$)$_2$, —P(OR$^A$)$_2$, and P(RB)$_2$, wherein R' is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical, P(O)(OR$^A$)$_2$, —P(OR$^A$)$_2$, and P(R$^B$)$_2$; or OR' is an optionally substituted saturated or unsaturated, nonaromatic or aromatic heterocyclic radical;

R" and R'" are each independently of one another H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or NR"R'" is an optionally substituted saturated or unsaturated, nonaromatic or aromatic heterocyclic radical;

R"" are each independently of one another H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or SR" is an optionally saturated or unsaturated, nonaromatic or aromatic heterocyclic radical;

$R^A$ is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;

$R^B$ is H, halogen, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;

wherein at least one of $R^2$ and $R^4$ on each phenyl ring is not hydrogen.

Another embodiment of this aspect of the invention is the atropisomeric 1,8-bisphenolnaphthalene compounds of formula (I), wherein $R^1$ and $R^5$ are independently selected from the group consisting of hydrogen, ($C_1$-$C_6$) alkyl, ($C_2$-$C_6$) alkenyl, ($C_2$-$C_6$) alkynyl, ($C_3$-$C_9$) cycloalkyl, aryl, benzyl, heterocyclyl, heteroaryl, chloro, bromo, iodo, ($C_1$-$C_6$) acyl, amino, amido, azido, cyano, formyl, carbamoyl, —$SF_5$, nitro, OR', NR"R'", SR"", P(O)(OR$^A$)$_2$, —P(OR$^A$)$_2$, and P(RB)$_2$, wherein R' is H, ($C_1$-$C_6$) alkyl, ($C_2$-$C_6$) alkenyl, ($C_2$-$C_6$) alkynyl, ($C_3$-$C_6$) cycloalkyl or ($C_5$-$C_6$) cycloalkenyl, an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, preferably 1 to 12 carbon atoms, in particular 1 to 8 carbon atoms, P(O)(OR$^A$)$_2$, —P(OR$^A$)$_2$, and P(R$^B$)$_2$; or OR' is a saturated or unsaturated, nonaromatic or aromatic heterocyclic radical having 3 to 9 ring atoms and 1 to 4 hetero ring atoms with at least the oxygen from OR' being a hetero ring atom, where the further hetero ring atoms optionally present in addition to the nitrogen atom are selected from the group consisting of N, O and S and the radical is unsubstituted or substituted; or R" and R'" are each independently of one another H, ($C_1$-$C_6$)alkyl, ($C_2$-$C_6$)alkenyl, ($C_2$-$C_6$)alkynyl, ($C_3$-$C_6$)cycloalkyl or ($C_5$-$C_6$)cycloalkenyl, or an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, preferably 1 to 12 carbon atoms, in particular 1 to 8 carbon atoms; or NR"R'" is a saturated or unsaturated, nonaromatic or aromatic heterocyclic radical having 3 to 9 ring atoms and 1 to 4 hetero ring atoms with at least the nitrogen from NR'R" being a hetero ring atom, where the further hetero ring atoms optionally present in addition to the nitrogen atom are selected from the group consisting of N, O and S and the radical is unsubstituted or substituted; or R"" is H, ($C_1$-$C_6$)alkyl, ($C_2$-$C_6$)alkenyl, ($C_2$-$C_6$)alkynyl, ($C_3$-$C_6$)cycloalkyl or ($C_5$-$C_6$)cycloalkenyl, or an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, preferably 1 to 12 carbon atoms, in particular 1 to 8 carbon atoms, or SR"" is a saturated or unsaturated, nonaromatic or aromatic hetrocyclic radical having 3 to 9 ring atoms and 1 to 4 hetero ring atoms with at least the sulfur from SR' being a hetero ring atom, where the further hetero ring atoms optionally present in addition to the nitrogen atom are selected from the group consisting of N, O and S and the radical is unsubstituted or substituted;

$R^A$ is H, or $(C_1-C_6)$ alkyl;

$R^B$ is H, halogen, or $(C_1-C_6)$ alkyl;

wherein at least one of $R^1$ and $R^5$ on each phenyl ring is not hydrogen;

$R^2$, $R^3$, $R^4$, $R^6$, $R^7$ and $R^8$ are independently selected from the group consisting of hydrogen, $(C_1-C_6)$ alkyl, $(C_2-C_6)$ alkenyl, $(C_2-C_6)$ alkynyl, $(C_3-C_9)$ cycloalkyl, aryl, benzyl, heterocyclyl, heteroaryl, chloro, bromo, iodo, $(C_1-C_6)$ acyl, amino, amido, azido, cyano, formyl, carbamoyl, $-SF_5$, nitro, OR', NR"R''', SR'''', $P(O)(OR^A)_2$, $-P(OR^A)_2$, and $P(RB)_2$, wherein R' is H, $(C_1-C_6)$ alkyl, $(C_2-C_6)$ alkenyl, $(C_2-C_6)$ alkynyl, $(C_3-C_6)$ cycloalkyl or $(C_5-C_6)$ cycloalkenyl, an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, preferably 1 to 12 carbon atoms, in particular 1 to 8 carbon atoms, $P(O)(OR^A)_2$, $-P(OR^A)_2$, and $P(R^B)_2$; or OR' is a saturated or unsaturated, nonaromatic or aromatic heterocyclic radical having 3 to 9 ring atoms and 1 to 4 hetero ring atoms with at least the oxygen from OR' being a hetero ring atom, where the further hetero ring atoms optionally present in addition to the nitrogen atom are selected from the group consisting of N, O and S and the radical is unsubstituted or substituted; or R" and R''' are each independently of one another H, $(C_1-C_6)$alkyl, $(C_2-C_6)$alkenyl, $(C_2-C_6)$alkynyl, $(C_3-C_6)$cycloalkyl or $(C_5-C_6)$cycloalkenyl, or an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, preferably 1 to 12 carbon atoms, in particular 1 to 8 carbon atoms; or NR"R''' is a saturated or unsaturated, nonaromatic or aromatic heterocyclic radical having 3 to 9 ring atoms and 1 to 4 hetero ring atoms with at least the nitrogen from NR'R" being a hetero ring atom, where the further hetero ring atoms optionally present in addition to the nitrogen atom are selected from the group consisting of N, O and S and the radical is unsubstituted or substituted; or R'''' is H, $(C_1-C_6)$alkyl, $(C_2-C_6)$alkenyl, $(C_2-C_6)$alkynyl, $(C_3-C_6)$cycloalkyl or $(C_5-C_6)$cycloalkenyl, or an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, preferably 1 to 12 carbon atoms, in particular 1 to 8 carbon atoms, or SR'''' is a saturated or unsaturated, nonaromatic or aromatic heterocyclic radical having 3 to 9 ring atoms and 1 to 4 hetero ring atoms with at least the sulfur from SR' being a hetero ring atom, where the further hetero ring atoms optionally present in addition to the nitrogen atom are selected from the group consisting of N, O and S and the radical is unsubstituted or substituted;

$R^A$ is H, or $(C_1-C_6)$ alkyl;

$R^B$ is H, halogen, or $(C_1-C_6)$ alkyl;

wherein at least one of $R^2$ and $R^4$ on each phenyl ring is not hydrogen.

Another embodiment of this aspect of the invention is the atropisomeric 1,8-bisphenolnaphthalene compounds of formula (I), wherein $R^1$ and $R^5$ are independently selected from the group consisting of hydrogen, $(C_1-C_4)$ alkyl, phenyl, chloro, bromo and iodo, wherein at least one of $R^1$ and $R^5$ on each phenyl ring is not hydrogen;

$R^2$ and $R^4$ are independently selected from the group consisting of hydrogen, $(C_1-C_4)$ alkyl, $(C_2-C_4)$ alkenyl, $(C_2-C_4)$ alkynyl, $(C_3-C_6)$ cycloalkyl, phenyl, $(C_1-C_6)$ acyl, and formyl, wherein at least one of $R^2$ and $R^4$ on each phenyl ring is not hydrogen;

$R^3$ is independently $PR'_2$, $NR'_2$ or OR' wherein each R' is independently H or $(C_1-C_4)$ alkyl, and $R^6$, $R^7$ and $R^8$ are independently selected from the group consisting of hydrogen, $(C_1-C_4)$ alkyl, hydroxyl, $(C_1-C_4)$ alkoxy, halogen, $NH_2$, amido, azido, cyano, formyl, carbamoyl, nitro.

Another embodiment of this aspect of the invention is the atropisomeric 1,8-bisphenolnaphthalene compounds of formula (I), wherein $R^1$ and $R^5$ are independently selected from the group consisting of hydrogen, $(C_1-C_4)$ alkyl, phenyl, chloro, bromo and iodo, wherein at least one of $R^1$ and $R^5$ on each phenyl ring is not hydrogen;

$R^2$ and $R^4$ are independently selected from the group consisting of hydrogen, $(C_1-C_4)$ alkyl, $(C_2-C_4)$ alkenyl, $(C_2-C_4)$ alkynyl, $(C_3-C_6)$ cycloalkyl, phenyl, $(C_1-C_6)$ acyl, and formyl, wherein at least one of $R^2$ and $R^4$ on each phenyl ring is not hydrogen;

$R^3$ is independently OR' wherein R' is H or $(C_1-C_4)$ alkyl; and $R^6$, $R^7$ and $R^8$ are independently selected from the group consisting of hydrogen, $(C_1-C_4)$ alkyl, hydroxyl, $(C_1-C_4)$ alkoxy, halogen, $NH_2$, amido, azido, cyano, formyl, carbamoyl, nitro.

Another embodiment of this aspect of the invention is the atropisomeric 1,8-bisphenolnaphthalene compounds of formula (I), wherein $R^1$ and $R^5$ are independently H and methyl, wherein at least one of $R^1$ and $R^5$ on each phenyl ring is not hydrogen;

$R^2$ and $R^4$ are independently phenyl or formyl, wherein at least one of $R^2$ and $R^4$ on each phenyl ring is not hydrogen;

$R^3$ is independently OR' wherein R' is H or methyl; and $R^6$, $R^7$ and $R^8$ are independently selected from the group consisting of hydrogen and methyl.

In another aspect of the invention, the compounds of formula (I) are stable to racemization at room temperature (20-25° C.).

Another aspect of the invention relates to the process of making the atropisomeric 1,8-bisphenolnaphthalene compounds of formula (I).

One embodiment of this aspect of the invention is where the process comprises of:

(a) reacting a compound of formula (II):

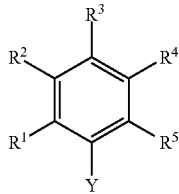

(II)

wherein $R^1$, $R^2$, $R^3$, $R^4$ and $R^5$ are as defined above and Y is a boron- or metal-based moiety
with a compound of formula (III)

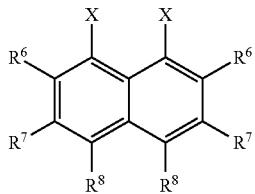

(III)

wherein $R^6$, $R^7$ and $R^8$ are as defined above and X is a displaceable group to form the compounds of formula (I); and (b) optionally, if $R^3$ is not hydroxyl after step (a), deprotecting or hydrolyzing $R^3$ to form the compound of formula (I) wherein $R^3$ is hydroxyl.

In another embodiment of this aspect of the invention, Y is a boron based moiety and X is selected from the group consisting of chlorine, bromine, iodine, phenylsulfonate, tosylate and triflate.

In another embodiment of this aspect of the invention, Y is selected from the group consisting of $B(OH)_2$, 9-BBN, $B(CHCH_3CH(CH_3)_2)_2$.

In another embodiment of this aspect of the invention, is where the process is by way of a process selected from the group consisting of Suzuki coupling, Stille coupling, Negishi coupling and Kumada coupling.

In another embodiment of this aspect of the invention, the process results in a ratio of syn- and anti-isomers for the compounds of formula (I) selected from the ranges consisting of about 1:1 to about 1:8, about 1:2 to about 1:6 and about 1:3 to about 1:4

In another embodiment of this aspect of the invention, the process results in % de (% diastereomeric excess) for the compounds of formula (I) selected from the ranges consisting of >95%, >98% and >99%. Note that >99% is effectively complete stereochemical purity In another embodiment of this aspect of the invention, the moieties represented by variables $R^6$-$R^8$ can be synthesized after forming the atropisomeric 1,8-bisphenolnaphthalene compounds of formula (I) with the above definition of variables $R^1$-$R^5$ by derivitization techniques known to those of skill in the art (see e.g. *March's Advanced Organic Chemistry—Reactions, Mechanisms and Structure* (6th Edition), Michael B. Smith and Jerry March, Wiley-Interscience (2007); *Modern Synthetic Reactions* (Second Edition), Herbert House, W.A. Benjamin, Inc. (1972)).

Another aspect of the invention relates to the process of converting one conformer of the atropisomeric 1,8-bisphenolnaphthalene compounds of formula (I) into another conformeric form.

In one embodiment of this aspect of the invention, a conformer of the atropisomeric 1,8-bisphenolnaphthalene compounds of formula (I) obtained from the described process of making is converted to another conformer by dissolving the conformer of the compound of formula (I) in a solvent and heating. In another embodiment of the invention, the heating can be performed from room temperature to a temperature range selected from the group consisting of about 35° C. to less than the boiling point of the solvent; about 35° C. to about 95° C. and about 40° C. to about 65° C. To facilitated the heating and conversion process, the compounds of formula (I) can be dissolved using known techniques in the art, e.g. such as those described in *Vogel's Textbook of Practical Organic Chemistry* (Fifth Edition), Furniss et al., Longman Scientific & Technical (1989)).

Another aspect of the invention relates to a process of separating enantiomers from a racemic mixture of atropisomeric 1,8-bisphenolnaphthalene compounds of formula (I).

In one embodiment of this aspect of the invention, a racemic mixture of atropisomeric 1,8-bisphenolnaphthalene compounds of formula (I) is allowed to react with a chiral compound to form a diastereomeric adduct.

In another embodiment of this aspect of the invention, $R^2$ and $R^4$ of formula (I) are independently selected from the group consisting of carboxy, amide, —CHO, —(CO)alkyl, (C=NH)alkyl and amidino.

In another embodiment of this aspect of the invention, the chiral compound is an amine, an amide, a carboxylic acid, an amino alcohol or an alcohol.

In another embodiment of this aspect of the invention, the chiral compound is an amine or an amino alcohol.

In another embodiment of this aspect of the invention, the chiral compound is an amino alcohol.

In another embodiment of this aspect of the invention, diasteriomeric adducts are formed by condensing the racemic mixture of atropisomeric 1,8-bisphenolnaphthalene compounds of formula (I) with a chiral amine or amino alcohol to form a diimine product.

In another embodiment of this aspect of the invention, the chiral amino alcohol is selected from the group consisting of 2-amino-1-propanol, 2-amino-4-methyl-1-pentanol, ephedrine or pseudoephedrine.

In another embodiment of this aspect of the invention, the mixture of diasteriomeric adducts are heated to allow the interconversion between the diastereomers, which results in a diastereomeric adduct of formula (I) with a % diasteriomeric excess (% de) selected from the ranges consisting of >90%, >95%, >98% and >99%.

In another embodiment of this aspect of the invention, the diastereomers of the diastereomeric adduct of formula I are separated chromatographically, which results in a diastereomeric adduct of formula I with a % diasteriomeric excess (% de) selected from the ranges consisting of >90%, >95%, >98% and >99%.

In another embodiment of this aspect of the invention, the diasteriomeric adduct is cleaved to yield an atropisomeric 1,8-bisphenolnaphthalene compound of formula (I) with % enantiomeric excess (% ee) selected from the ranges consisting of >90%, >95%, >98% and >99%. Note that >99% is effectively complete stereochemical purity.

In another embodiment of this aspect of the invention, the cleavage of the diasteriomeric adduct is accomplished by hydrolysis to yield an atropisomeric 1,8-bisphenolnaphthalene compound of formula (I) with % enantiomeric excess (% ee) selected from the ranges consisting of >90%, >95%, >98% and >99%.

Another aspect of the invention relates to a method of providing enantiomeric recognition between stereoisomers of a chiral compound which comprises of adding an atropisomeric 1,8-bisphenolnaphthalene compounds of formula (I) to a solution containing a racemic or diasteriomeric mixture of the chiral compound.

In one embodiment of this aspect of the invention, the chiral compound is an amine, amino alcohol amino acid or alcohol.

In another embodiment of the invention, the chiral compound is an amine.

In another embodiment of the invention, the chiral amine is selected from the group consisting of 1-phenylethylamine, 3,3-dimethylbutan-2-amine, 3-dimethylbutan-2-amine, cyclohexane-1,2-diamine, 1,2-diphenylethane-1,2-diamine, 1,1-diphenylpropan-2-amine, 1-cyclohexylethanamine, 2,6,6-trimethylbicyclo[3.1.11]heptan-3-amine, and heptan-2-amine.

In another embodiment of this aspect of the invention, the atropisomeric 1,8-bisphenolnaphthalene compounds of formula (I) is 2.

Another aspect of the invention relates to a method of conducting asymmetric synthesis of a compound which comprising of adding an atropisomeric 1,8-bisphenolnaphthalene compounds of formula (I).

Further details related to the aspects and embodiments of the invention follow below.

In continuation of previously conducted studies with stereodynamic chiral biaryls and triaryls, (See (a) Wolf, C.; Ghebramariam, B. T. *Tetrahedron: Asymm.* 2002, 13, 1153-1156. (b) Wolf, C.; Tumambac, G. E. *J. Phys. Chem. A.* 2003, 107, 815-817. (c) Tumambac, G. E.; Wolf, C. *J. Org. Chem.* 2004, 69, 2048-2055. (d) Tumambac, G. E.; Mei, X.; Wolf, C. *Eur. J. Org. Chem.* 2004, 3850-3856. (e) Wolf, C. *Chem. Soc. Rev.* 2005, 34, 595-608. (f) Tumambac, G. E.; Wolf, C. *J. Org. Chem.* 2005, 70, 2930-2938. (g) Wolf, C.; Xu, H. *Tetrahedron Lett.* 2007, 48, 6886-6889.) and 1,8-diheteroarylnaphthalene-derived sensors, ((a) Mei, X.; Wolf, C. *Chem. Commun.* 2004, 2078-2079. (b) Mei, X.; Wolf, C. *J. Am. Chem. Soc.* 2004, 126, 14736-14737. (c) Tumambac, G. E.; Wolf, C. *Org. Lett.* 2005, 7, 4045-4048. (d) Mei, X.; Martin, R. M.; Wolf, C. *J. Org. Chem.* 2006, 71, 2854-2861. (e) Liu, S.; Pestano, J. P. C.; Wolf, C. *J. Org. Chem.* 2008, 73, 4267-4270. (f) Mei, X.; Wolf, C. *Tetrahedron Lett.* 2006, 47, 7901-7904. (g) Wolf, C.; Liu, S.; Reinhardt, B. C. *Chem. Commun.* 2006, 4242-4244. (h) Mei, X.; Wolf, C. *J. Am. Chem. Soc.* 2006, 128, 13326-13327.) 1,8-bis(3'-formyl-4'-hydroxyphenyl)naphthalene, 1, exhibiting two salicylaldehyde rings in the peri-positions of naphthalene was prepared via Suzuki coupling of 1,8-diiodonaphthalene and boronic acid followed by deprotection of dialdehyde 3 (Scheme 1). (See (a) Watkinson, M.; Whiting, A.; McAuliffe, C. A. *J. Chem. Soc., Chem. Commun.* 1994, 2141. (b) Ghosn, M. W.; Wolf, C. *J. Am. Chem. Soc.* 2009, 131, 16360-16361.)

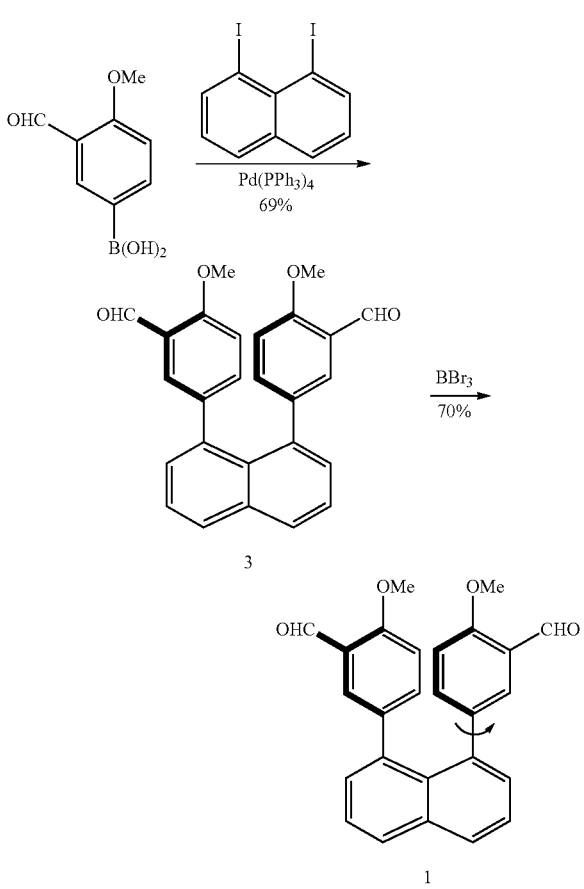

Scheme 1. Synthesis of 1,8-bis(3'-formyl-4'-hydroxyphenyl)naphthalene, 1.

Triaryl 1 undergoes fast rotation about the two aryl-aryl bonds at room temperature, which results in the interconversion of the enantiomeric anti-isomers via the thermodynamically less stable meso syn-intermediate. We realized that imine formation with amino alcohols disturbs this equilibrium and strongly favors population of a single diastereomer that is stabilized by intramolecular hydrogen bonding (Scheme 2). The diimine formed displays strong Cotton effects at high wavelengths and NMR and crystallographic analysis showed that the central chirality of the amino alcohol substrate induces a rigid, axially chiral triaryl scaffold with perfect stereocontrol: Condensation of 1 and (R)-amino alcohols results in well-defined amplification of asymmetric induction and the triaryl was found to adopt an (M,M)-conformation. The opposite sense of chiral induction was observed with (S)-amino alcohols. We were able to demonstrate that the fast diimine formation, which is complete within 5 minutes, followed by in situ CD measurements allows time-efficient determination of the absolute configuration and the enantiomeric purity of the substrate used. Similar results were obtained with amino acids. (See Ghosn, M. W.; Wolf, C. *Tetrahedron* 2010, 66, 3989-3994.)

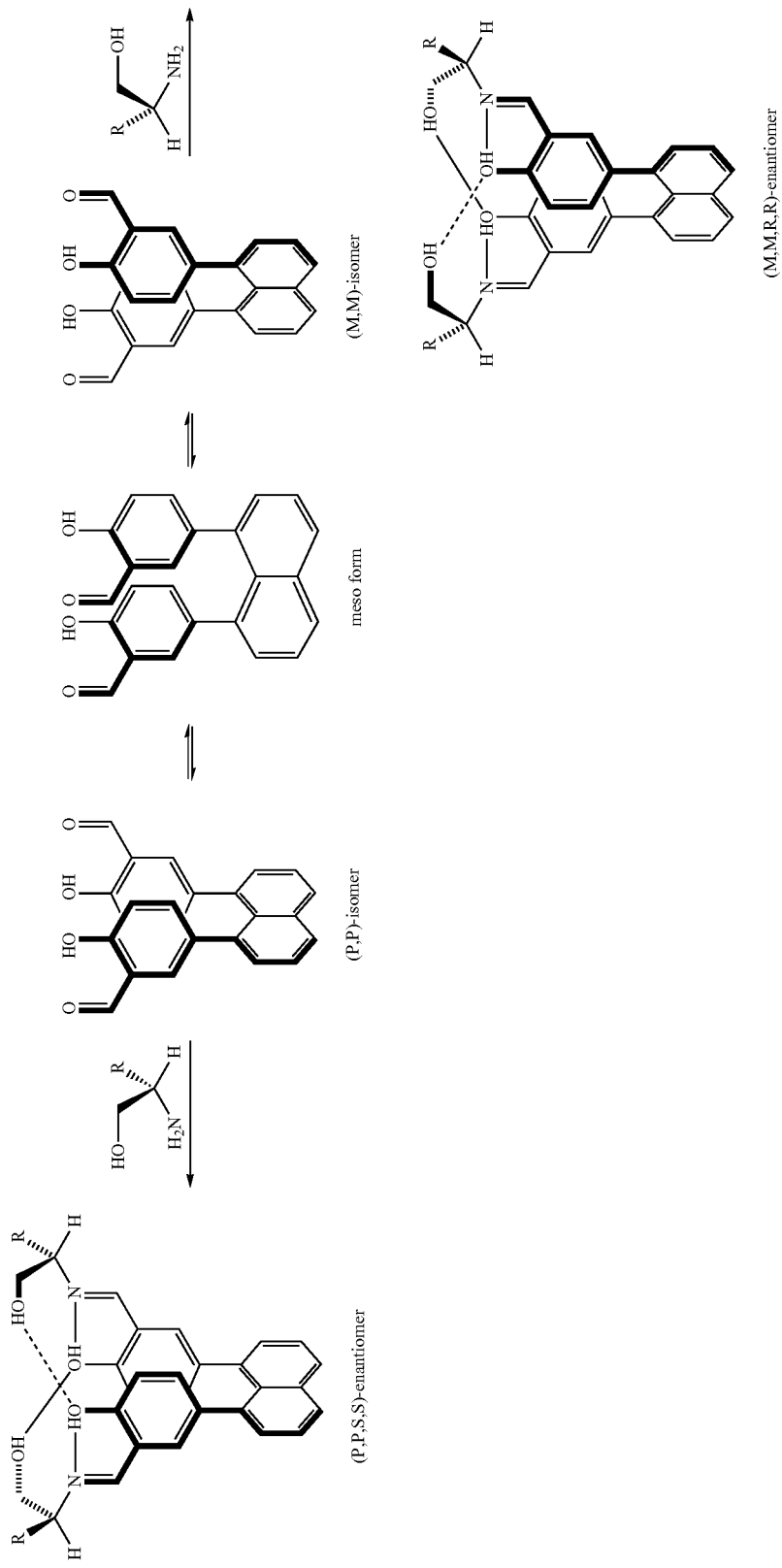
Scheme 2. Central-to-axial chirality induction upon diimine formation with stereodynamic triaryl 1.

We envisioned that a less fluxional analogue of 1 would provide further insights into (a) the amplification of asymmetric induction, (b) the effect of the intramolecular hydrogen bonding on the conformational stability of the diimine derivatives and (c) provide an entry to the potential use of these compounds in enantioselective recognition and catalysis. Since Clough and Roberts estimated the energy barrier to syn/anti-diastereomerization of 1,8-bis(2-methylphenyl)naphthalene, 4a, as approximately 100 kJ/mol, (Clough, R. L.; Roberts, J. D. *J. Am. Chem. Soc.* 1976, 98, 1018-1020.) we expected that incorporation of methyl groups into the ortho-positions of 1 would produce conformational isomers that are stable to interconversion and separable at room temperature (Scheme 3). We therefore decided to prepare 1,8-bis(2'-methyl-4'-hydroxy-5'-formylphenyl)naphthalene, 5, exhibiting moderate bulk adjacent to the chiral axes which should suffice to isolate and characterize the stereoisomers of this atropisomer and its diimine derivatives while racemization and diastereomerization reactions could be studied at elevated temperatures.

Scheme 3. Structures of 4a exhibiting anti-parallel (anti-isomer) and parallel (syn-isomer) 2-methylphenyl moieties and of 5.

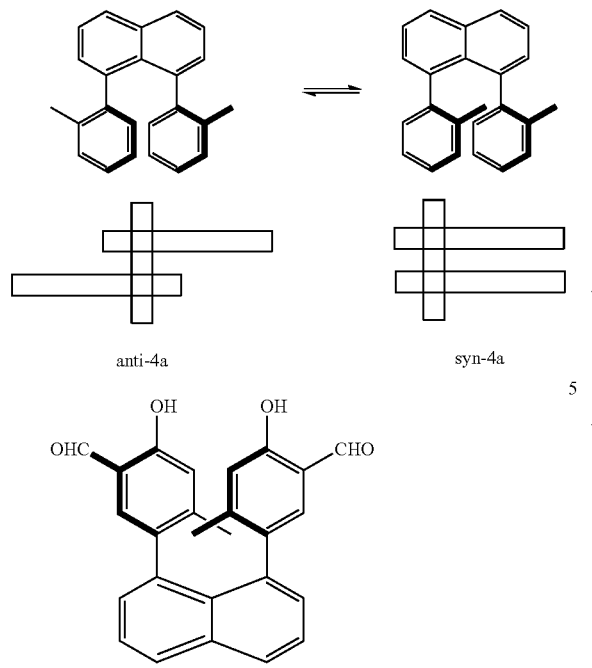

Based on our experience with the synthesis and atropisomerization of chiral biaryls and triaryls, (E.g., Wolf, C.; Ghebramariam, B. T. *Tetrahedron: Asymm.* 2002, 13, 1153-1156.) and 1,8-diheteroarylnaphthalene-derived sensors, (E.g., Mei, X.; Wolf, C. *Chem. Commun.* 2004, 2078-2079.) we found that incorporation of steric bulk proximate to the aryl-aryl bonds in axially chiral 1,8-bisphenolnaphthalenes affords isolable enantiomers (FIG. 1). We believe that this finding will have important implications to chiral ligand development for asymmetric catalysis, recognition and other fields. We now wish to report the first example of an application of a conformationally stable, axially chiral 1,8-bisphenolnaphthalene, such as 2 and 5.

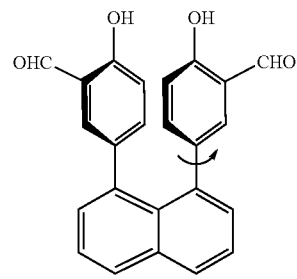

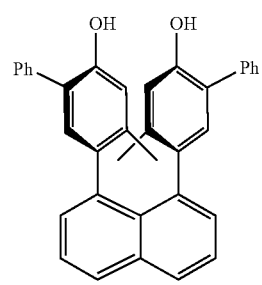

Structures of axially chiral 1,8-bisphenolnaphthalenes

We began the synthesis of 5 with Suzuki coupling of 1,8-diiodonaphthalene and commercially available 4-methoxy-2-methylphenylboronic acid (Scheme 4). Initially, we screened the effect of various catalysts, solvents, base and temperature to identify suitable reaction conditions for the construction of the sterically congested scaffold of 5. We were pleased to find that 1,8-bis(2'-methyl-4'-methoxyphenyl)naphthalene, 4, can be obtained in quantitative amounts using $Pd(PPh_3)_4$ as catalyst and $K_3PO_4$ as base in toluene. NMR analysis revealed that 4 was a 1:3 mixture of the syn- and anti-isomers. The Vilsmeier reaction with excess of phosphorous oxychloride and dimethyl formamide then furnished 1,8-bis(2'-methyl-4'-methoxy-5'-formylphenyl)naphthalene, 8, with 99% yield in approximately the same diastereomeric ratio. Finally, deprotection with boron tribromide gave 5 having a syn- and anti-isomer ratio of 1:4 in 77% yield.

Scheme 4. Synthesis of 1,8-bis(2'-methyl-4'-hydroxy-5'-formylphenyl)naphthalene 5.

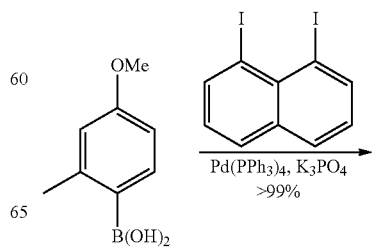

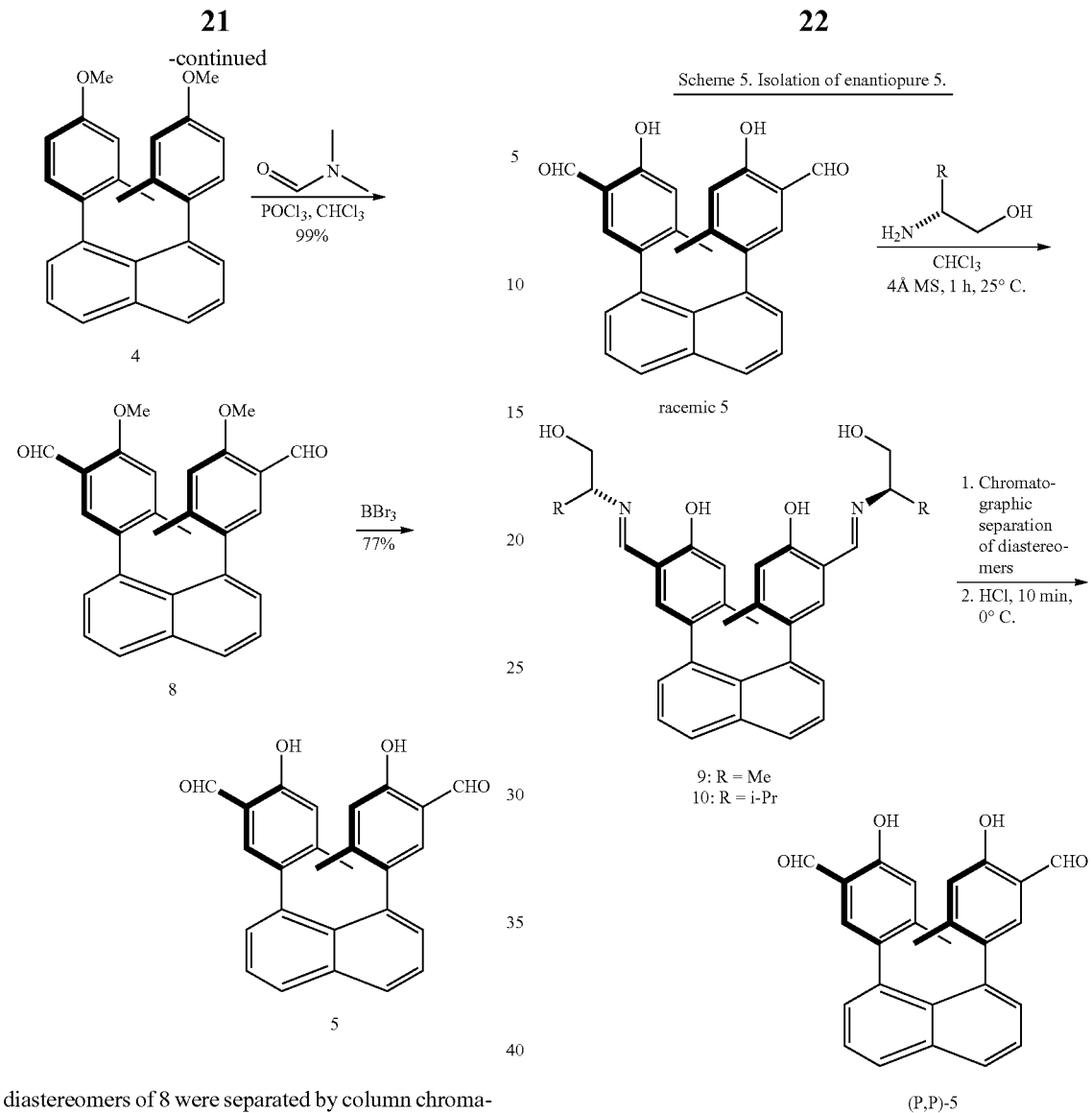

The diastereomers of 8 were separated by column chromatography and the racemic anti-isomer was converted to anti-5 and then to (P,P,R,R)-9 and (M,M,R,R)-9 by condensation with 2 equivalents of (R)-2-amino-1-propanol. The diimine formation proceeds with quantitative yields and is completed at room temperature within one hour. Chromatographic purification on silica gel then allowed isolation of the two diastereomeric products (Scheme 5). Heating of the diastereomeric mixture of 9 to establish thermodynamic equilibrium showed that the first eluted diimine corresponds to the more stable diastereomer, see below. The sense of amplification of asymmetric induction observed with the diimines of 1 and CD and crystallographic analysis of 5 and 9 suggest that (P,P,R,R)-9 is the thermodynamically favored atropisomer. Hydrolysis of (P,P,R,R)-9 with aqueous HCl at 0° C. afforded enantiopure (P,P)-5 in 85% yield, with no trace of the syn-diastereomer based on NMR analysis. The enantiopurity of 5 was confirmed by derivatization to the corresponding (P,P,R,R)-diimine with (R)-2-amino-1-propanol and NMR analysis did not show any signals of the diastereomeric (M,M,R,R)-isomer.

Based on our experience with stereolabile 1, which spontaneously adopts a single conformation upon diimine formation with enantiopure amino alcohols and the kinetic analysis of 4a by Clough and Roberts, we investigated the possibility to convert the atropisomeric mixture of 9 to a single isomer upon heating. Such an asymmetric transformation of the first kind would generate the thermodynamically favored diimine isomer and thus facilitate the formation of enantiopure 5 with a theoretical yield of 100% and without the need for an elaborate chromatographic separation of the equimolar mixture of (M,M,R,R)- and (P,P,R,R)-9. Several cases in which asymmetric transformation of the first kind was used to manipulate the diastereomeric ratio of axially chiral compounds have been reported. For example, Meyers et al. found that the stereochemical outcome of the diastereoselective oxazoline-mediated asymmetric Ullmann coupling of aryl bromides is significantly improved upon heating of the product mixture. (E.g., Nelson, T. D.; Meyers, A. I. *Tetrahedron Lett.* 1993, 34, 3061-3062.) This transformation favors the formation of the desired (P)-atropisomer, a key intermediate for the total synthesis of permethylated tellimagrandin. (Nelson, T. D.; Meyers, A. I. *J. Org. Chem.* 1994, 59, 2577-2580.) The same principle has been used for the deracemization of ortho-dihydroxylated biaryl ligands VANOL and VAPOL (E.g., Zhang, Y.; Yeung. S.-M.; Wu, H.; Heller, D. P.; Wu, C.; Wulff, W. D. *Org. Lett.* 2003, 5, 1813-1816.) and for the preparation of the aglycon of vancomycin. (E.g., Evans, D. A.; Wood, M. R.; Trotter, B. W.; Richardson, T. I.; Barrow, J. C.; Katz, J. L. *Angew. Chem., Int. Ed.* 1998, 37, 2700-2704.)

We realized that (M,M,R,R)- and (P,P,R,R)-9, formed from racemic 5 and (R)-2-amino-1-propanol at 25° C., showed distinct NMR spectra, for example two doublets at 1.26 and 1.40 ppm corresponding to the imino alcohol methyl groups (FIG. 1). We therefore used NMR analysis to monitor the atropisomerization process. Upon heating to 60.0° C., the signals of the thermodynamically less favored diastereomer decreased in intensity and (P,P,R,R)-9 with >98% de was obtained after 14 hours (see FIG. 1).

Figure 2:
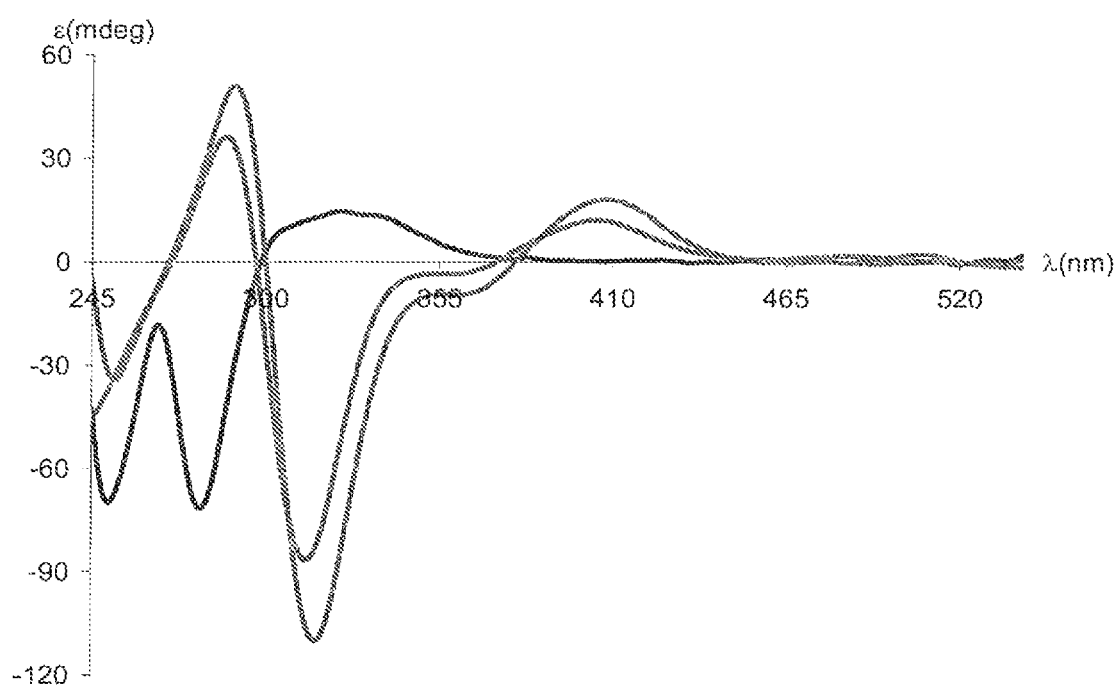
FIG. 2 depicts a CD spectra of (P,P)-5 (blue), (P,P,R,R)-9 (red) and (P,P,S,S)-9 (green) at $5.0 \times 10^{-5}$ M in CHCl$_3$.

We previously reported that condensation of stereolabile 1 and (R)-2-amino-1-propanol exclusively generates the (M,M,R,R)-stereoisomer which is the thermodynamically favored conformer due to stabilization by intramolecular hydrogen bonding and concomitant minimization of steric repulsion. Accordingly, diimine formation with (S)-2-amino-1-propanol gave the (P,P,S,S)-enantiomer, Scheme 2. These results are in perfect agreement with the asymmetric transformation of a mixture of (M,M,R,R)- and (P,P,R,R)-9 towards the latter diastereomer. In analogy to the amplification of asymmetric induction observed with 1, the central chirality of the imino alcohol moiety in 9 controls the chiral amplification and induces the same sense of axial chirality. (Note that the (M,M)-scaffold in 1 corresponds to the (P,P)-conformation in 5 and 9 because the presence of the ortho-methyl groups in the latter results in a change in the CIP priorities.) Since the atropisomerization occurs with more than 99% de, it provides quantitative access to stereochemically pure 9 on the gram scale, which can then be hydrolyzed without concomitant isomerization to enantiopure 5. Having developed a convenient procedure producing (P,P)-5, we were able to prepare (P,P,R,R)-9 and (P,P,S,S)-9, the thermodynamically less stable diastereomer, via condensation with either enantiomer of 2-amino-1-propanol. Analyzing the CD spectra of the enantiomeric (M,M,R,R)- and (P,P,S,S)-diimines of 1, we previously speculated that the Cotton effects are predominantly controlled by the sense of axial chirality while the chiral centers in the imino alcohol units were expected to have little or no effect on the chiroptical properties. Comparison of the CD spectra of (P,P)-5, (P,P,R,R)-9 and (P,P,S,S)-9, all exhibiting the same sense of axial chirality, now clearly shows that this assumption is correct (FIG. 2). The three atropisomers exhibit a pronounced positive Cotton effect, and the incorporation of the diimino alcohol units results in a significant red shift. Importantly, the diastereomeric (P,P)-diimines of 9 show almost perfectly superimposable CD spectra, which underscores the overwhelming or possibly exclusive contribution of the relative orientation of the two cofacial salicylidenimine rings to the observed CD activity. (It is noteworthy that the CD amplitudes of the less stable (P,P,S,S)-9 diastereomer are slightly diminished compared to (P,P,R,R)-9. This is probably due to noticeable atropisomerization of (P,P,S,S)-9 to its (M,M,S,S)-diastereomer, i.e. it is likely that the CD spectra obtained with (P,P,S,S)-9 and (P,P,R,R)-9 only differ because the former was not perfectly diastereomerically pure.)

Figure 3:
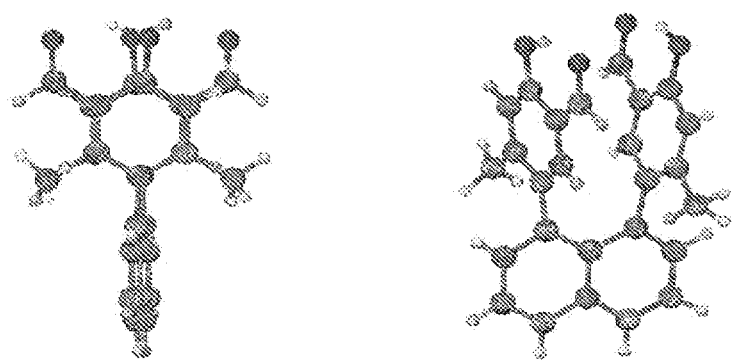
FIG. 3 depicts different views of the crystal structure of (P,P)-5.

Slow evaporation of a solution of enantiopure (P,P)-5 in chloroform gave single crystals suitable for X-ray studies (FIG. 3). As expected, crystallographic analysis shows that the two salicylaldehyde rings reside in almost perfectly perpendicular orientation relative to the naphthalene backbone, exhibiting a $C_2$-symmetric structure with a torsion angle of 5.32°. The splaying between the two phenyl rings was determined as 20.51° which results in a centroidal phenyl-to-phenyl separation of 3.47 Å. Based on the enforced π-stacking of the proximate salicylaldehyde rings, the positive Cotton effect and the large CD amplitudes of (P,P)-5 can be attributed to strong exciton coupling of the cofacial chromophores.

We then turned our attention to the kinetic analysis of 5 (Scheme 6). Interconversion of the stereoisomers of 5 requires one salicylaldehyde ring to rotate about the chiral naphthyl-phenyl axis. Accordingly, the edge of the rotating ring points towards the adjacent phenyl moiety in the transition state. In general, this process can proceed via two T-shaped transition states having the methyl group of the rotating phenyl ring either directed towards or away from the other phenyl ring. (Wolf, C. (Ed.) Dynamic Stereochemistry of Chiral Compounds, RSC, Cambridge, 2008, pp. 89.) The latter orientation is expected to afford significantly less steric hindrance and is therefore the favored interconversion pathway.

Scheme 6. Interconversion of the stereoisomers of 5.

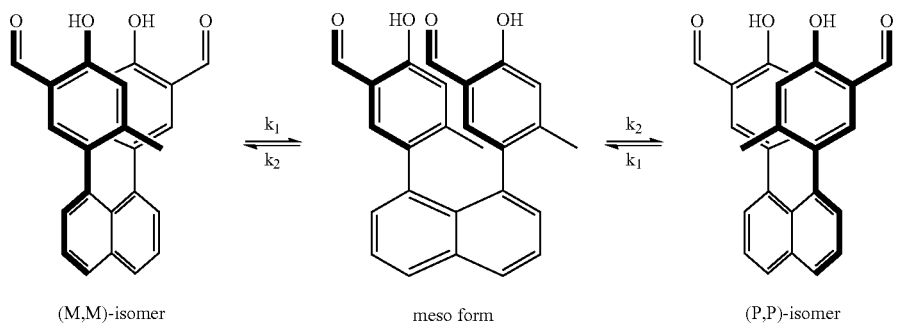

(M,M)-isomer       meso form       (P,P)-isomer

Figure 4:
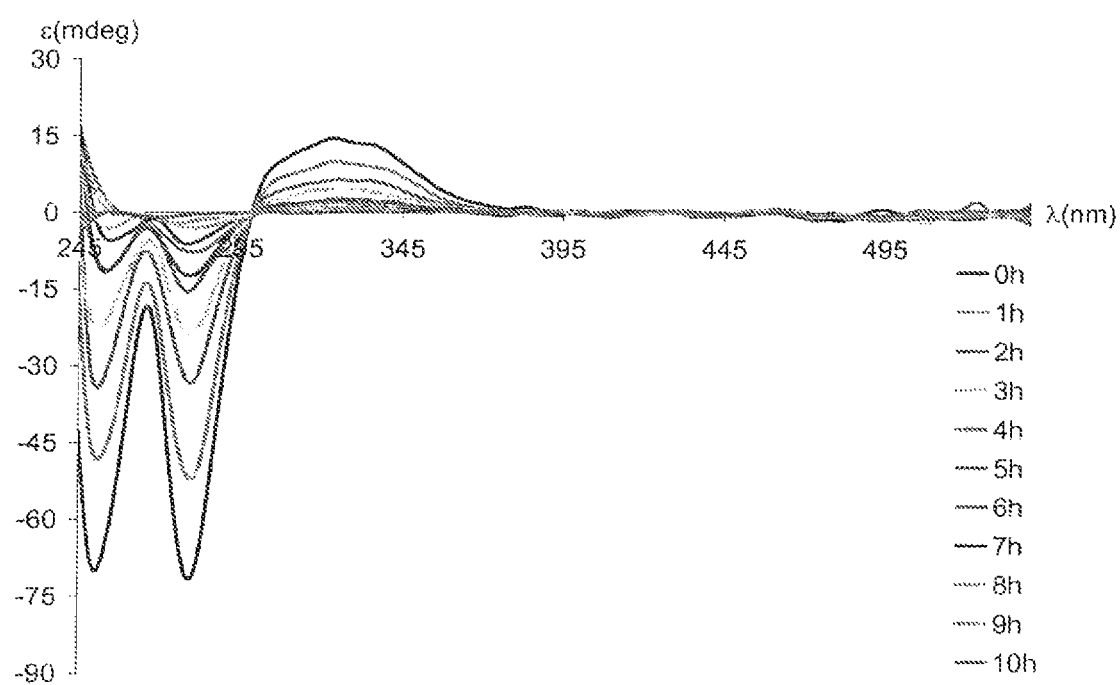
FIG. 4 depicts a decrease of the CD signal of (P,P)-5 as a result of racemization in chloroform ($6.95 \times 10^{-4}$ M) at 45.0° C. The CD spectra were collected at 25° C. at a concentration of $5.0 \times 10^{-5}$ M in chloroform.

A solution of (P,P)-5 in chloroform was stirred at 45.0° C. and small aliquots were taken at one hour intervals and diluted to $5.0 \times 10^{-5}$ M for CD analysis. After 10 hours, the CD signals disappeared indicating complete racemization (FIG. 4). The syn/anti-ratio of 5 at 45.0° C. in chloroform at equilibrium was determined by $^1$H-NMR spectroscopy as 23.4: 76.6. The observed ratio corresponds to a difference in Gibbs free energy of the anti- and syn-isomers, ΔG, of 1.3 kJ/mol according to the Boltzmann equation (1). (The factor 2 in equation 1 accounts for the two enantiomeric anti-isomers of 5.)

$$2N_{syn}/N_{anti} = \exp(-\Delta G°/RT) \tag{1}$$

Figure 5:
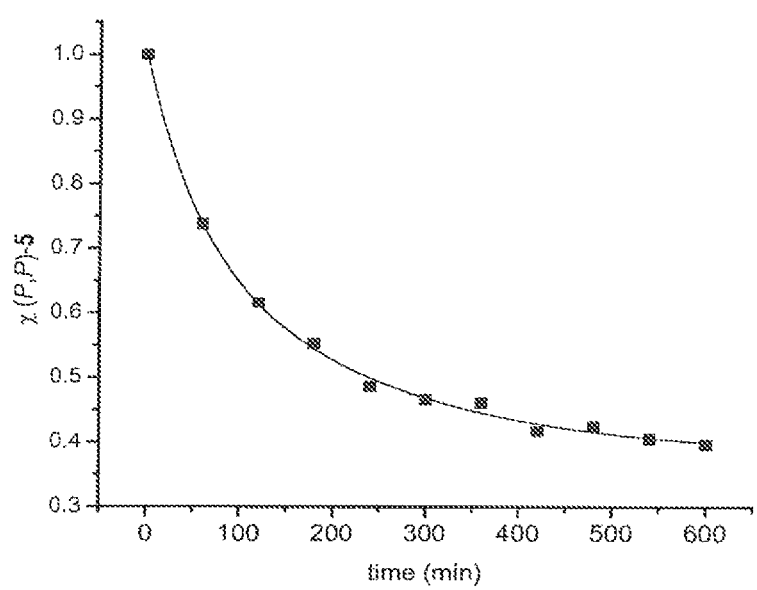
FIG. 5 depicts a change in the mole fraction of (P,P)-5 upon heating to 45.0° C. For conditions, see FIG. 4.

FIG. 5 shows the decrease of the mole fraction of (P,P)-5 as a function of time. The mathematical solution for the kinetics of consecutive, first-order, reversible reactions involving 3 species such as the syn/anti-interconversion of 5 has been reported by Vriens. (Vriens, G. N. *Ind. Eng. Chem.* 1954, 669-671.) Curve fit analysis using equation 2 allowed determination of the rate constant for the anti- to syn-isomerization, $k_1$.

$$x = C_1 e^{D_1 k_1 t} + C_2 e^{D_2 k_1 t} + \frac{\alpha}{K_1 K_2 E_2} \qquad (2)$$

$k_1$=rate constant of the anti- to syn-interconversion, $K_1$=equilibrium constant for the formation of the syn-isomer, $K_2$=equilibrium constant for the formation of either anti-isomer, $\alpha$=ratio of forward rate constants ($k_2/k_1$) for the consecutive, reversible, first-order reactions, $k_2$=rate constant for syn- to anti-interconversion, $C_1$, $C_2$, $D_1$, $D_2$, $E_2$ are constants.

Having determined the syn/anti-ratio and thus the equilibrium constant for the isomerization of 5, we were able to determine the rate constants for the reversible interconversion steps, $k_1$ and $k_2$, as $6.308 \times 10^{-5}$ s$^{-1}$ for the anti→syn- and as $1.038 \times 10^{-4}$ s$^{-1}$ for the syn→anti-interconversion, respectively. As expected, the observed isomerizations proved to obey first-order kinetics. Using the Eyring equation, the Gibbs activation energy, $\Delta G^{\neq}$, for the atropisomerization of 5 was calculated as 103.7 (102.4) kJ/mol for the conversion of the anti-(syn-) to the syn-(anti-)isomer (see SI).

The analysis of the atropisomerization of 9 is more complicated and involves four different rate constants (Scheme 7). Because CD analysis does not provide quantitative information about individual diastereomer concentrations we used NMR spectroscopy to monitor the conversion of (P,P,S,S)-9, which was prepared by condensation of (P,P)-5 with 2 equivalents of (S)-2-amino-1-propanol, to the thermodynamically stable atropisomer (M,M,S,S)-9 via the intermediate (M,P,S,S)-isomer.

of 8.8 kJ/mol. Crystallographic analysis of syn-9 and (P,P,R,R)-10 shows that these results can be explained by selective intramolecular hydrogen bonding and concomitant optimization of steric repulsion in (M,M,S,S)-9, vide infra. Following Vriens' mathematical treatment for two consecutive reversible reactions and curve fitting we then determined the individual rotational energy barriers (see SI for details). The interconversion of (P,P,S,S)-9 to the syn-diastereomer has a Gibbs activation energy, $\Delta G^{\neq}_{(P,P,S,S)-9 \to (P,M,S,S)-9}$, of 108.7 kJ/mol. The intermediate syn-isomer undergoes diastereomerization to the two anti-conformers and the corresponding activation energies were calculated as 106.3 kJ/mol ($\Delta G^{\neq}_{(P,M,S,S)-9 \to (P,P,S,S)-9}$) and 104.5 kJ/mol ($\Delta G^{\neq}_{(M,P,S,S)-9 \to (M,M,S,S)-9}$). As expected from the asymmetric transformation experiments discussed above, the energy barrier for the conversion of (M,M,S,S)-9 to the syn-isomer $\Delta G^{\neq}_{(M,M,S,S)-9 \to (M,P,S,S)-9}$, is significantly higher and was determined as 115.7 kJ/mol. To confirm these data, we analyzed the initial decay of (P,P,S,S)-9 at low conversion (less than 2% completion), which can be approximately treated as an irreversible first-order reaction (see Experimental Section). We thus obtained a rotational energy barrier, $\Delta G^{\neq}_{(P,P,S,S)-9 \to (M,P,S,S)-9}$, of 109.2 kJ/mol, which is in very good agreement with the value determined by curve fitting.

Figure 7:
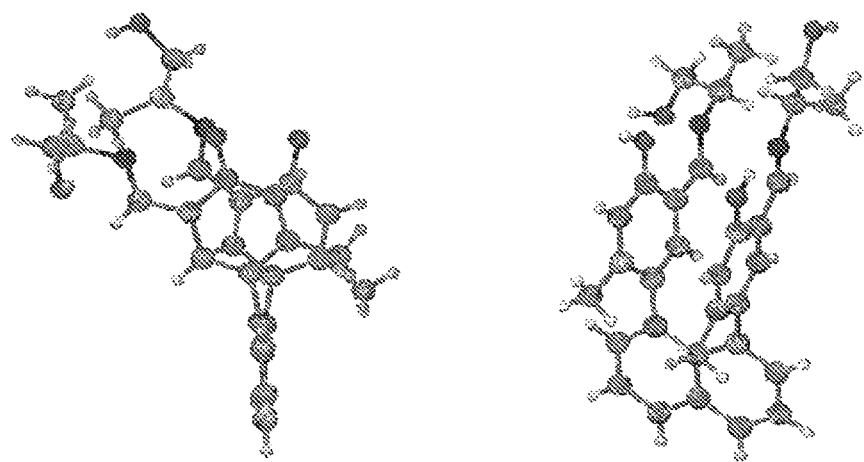
FIG. 7 depicts the single crystal structure of syn-9.

Attempts to grow a single crystal of (P,P,R,R)- or (M,M,S,S)-9 for crystallographic analysis were unsuccessful. But we were able to obtain a crystal structure of the syn-isomer (FIG. 7). This atropisomer has a torsion angle of 18.33° and the splaying between the two phenyl rings is 21.09° corresponding to a centroidal phenyl-to-phenyl separation of 3.52 Å. The steric repulsion between the two salicylidenimine rings explains the low relative stability compared to the (P,P,R,R)- or the (M,M,S,S)-isomer.

To better understand the overwhelming thermodynamic stability of the (P,P,R,R)- and the (M,M,S,S)-configuration, we decided to prepare the corresponding diimine using (R)-

Scheme 7. Interconversion of the atropisomers of 9.

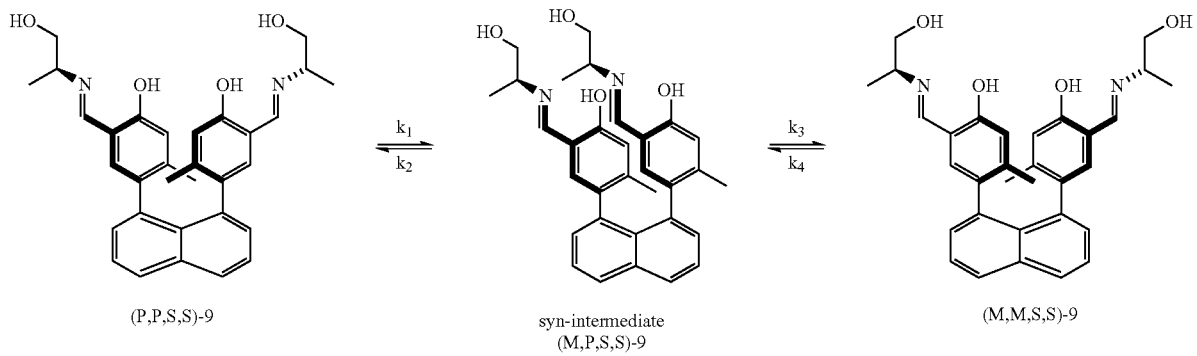

(P,P,S,S)-9 syn-intermediate
(M,P,S,S)-9

(M,M,S,S)-9

Figure 6:
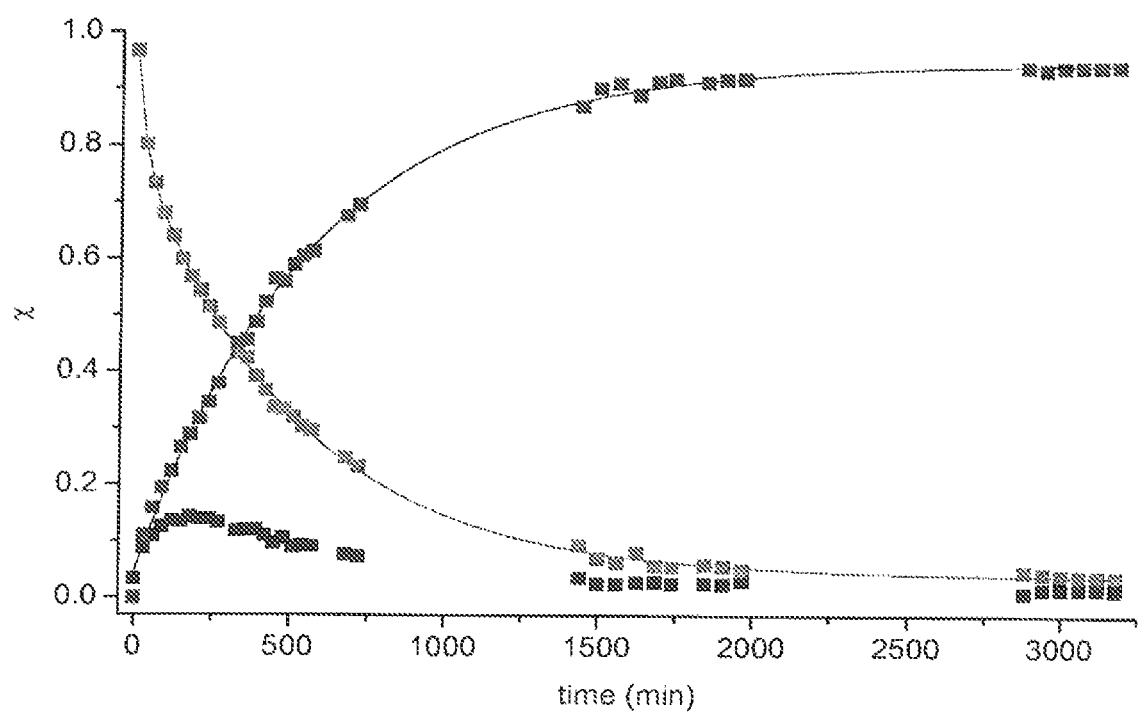
FIG. 6 depicts the analysis and curve fitting of the change in the mol fractions of (P,P,S,S)-9 (red), (M,P,S,S)-9 (black) and (M,M,S,S)-9 (blue) upon heating of (P,P,S,S)-9 to 58.0° C. in chloroform.
Figure 8:
FIG. 8 depicts different views of the crystal structure of (P,P,R,R)-10 showing the hydrogen bonding motif.

A solution of (P,P,S,S)-9 in deuterated chloroform was heated to 58.0° C. and the isomerization was studied by integration of the benzylic $^1$H NMR signals of the three diastereomers (see SI for details). Equilibrium was reached after 2 days, and the atropisomeric ratio was determined as 94.4:3.9:1.7 [(M,M,S,S):(P,P,S,S):(M,P,S,S)] (FIG. 6). Accordingly, the thermodynamically favored (M,M,S,S)-atropisomer is more stable than the syn-intermediate by 11.2 kJ/mol while conversion of the latter to (P,P,S,S)-9 is driven by only 2.4 kJ/mol. Comparison of the relative amounts of the two anti-isomers of 9 reveals a difference in Gibbs free energy 2-amino-3-methyl-1-butanol (see SI for details on the synthesis, CD analysis etc). Fortunately, a crystal of (P,P,R,R)-10 was obtained by crystallization from a hexane solution (FIG. 8). Crystallographic analysis revealed a torsion angle of 18.17° and splaying between the two phenyl rings was calculated as only 13.46° resulting in a centroidal phenyl-to-phenyl separation of 3.33 Å. The significantly reduced splaying compared to syn-9 is quite remarkable and results from reduced steric repulsion between the imino alcohol units and additional hydrogen bonding between the alcohol groups and the phenol units in the opposite salicylidenimine ring. The arrangement of the two salicylidenimines in (P,P,R,R)-10 allows formation of a total of four intramolecular hydrogen bonds (the phenol groups also undergo hydrogen bonding with the adjacent imines) while the steric bulk of the imino alcohol moieties is placed outside of this ring structure in the least crowded positions. The C=N • • • HOC$_{phenyl}$ and the C$_{aliph}$OH • • • OC$_{phenyl}$ hydrogen bond lengths are 1.861 and 2.178 Å, respectively.

In analogy to the results obtained with 9, we observed quantitative asymmetric transformation of the first kind with 10, which can be used to either prepare pure (M,M,S,S)- or (P,P,R,R)-atropisomers of these diimines. The kinetic and thermodynamic analyses of the unidirectional atropisomerization process of 9 and 10 discussed above and in the SI are in perfect agreement with the crystallographic data showing distinct stabilization of the (P,P,R,R)-isomer due to intramolecular hydrogen bonding and minimized steric repulsion between the imine moieties.

We also found that (P,P)-5 can be used for the kinetic resolution of the enantiomers of 2-amino-1-propanol. Diimine formation of the enantiopure dialdehyde 5 and 4 equivalents of the racemic substrate at room temperature followed by extraction after 5 hours allowed recovery of the remaining amino alcohol in 47% yield. Chiral HPLC analysis showed that the (S)-amino alcohol was enriched to 54% cc, which proves the expected favored formation of (P,P,R,R)-9 (see Experimental Section).

In conclusion, we have synthesized the first examples of axially chiral 1,8-bisphenolnaphthalenes that are stable to racemization at room temperature. The incorporation of two ortho-substituted phenol moieties into a rigid C$_2$-symmetric scaffold that is reminiscent of the successful BINOL motif has been of general interest due to potential applications in asymmetric catalysis and enantioselective sensing for a long time. Stereochemical analysis showed that the anti-stereoisomers of 1,8-bis(2'-methyl-4'-hydroxy-5'-formylphenyl)naphthalene, 5, and its diimine analogues 9 and 10 are significantly more stable than the corresponding syn-isomer. Slow syn/anti-interconversion, obeying reversible first-order kinetics, of 5, 9 and 10 occurs at elevated temperatures and this provides a convenient entry towards enantiopure bisphenols that can be prepared on the gram scale via asymmetric transformation of the first kind. Spectroscopic NMR and CD analyses supported by crystallography of syn- and anti-1,8-bisphenolnaphthalenes showed that the incorporation of two imino alcohol units into the triaryl scaffold controls the outcome of the unidirectional atropisomerization with literally perfect stereocontrol, resulting from a unique intramolecular hydrogen bonding motif and concomitant reduction of steric repulsion. While the stereochemical bias of the atropisomers studied originates from the central chirality of the incorporated amino alcohol units, the chiroptical properties are solely determined by the sense of axial chirality. Chiral recognition studies using 1,8-bisphenolnaphthalenes as UV, CD and fluorescence sensors are currently underway in our laboratories.

The invention will now be further described by way of the following non-limiting examples.

EXAMPLES

A. Experimental Procedures for Synthesizing 5, 9 and 10

All reagents and solvents were used without further purification. Reactions were carried out under nitrogen atmosphere and under anhydrous conditions. 1,8-Diiodonaphthalene was prepared from 1,8-diaminonaphthalene as described in the literature. (House, H. O.; Koepsella, D. G.; Campbel, W. J. J. Org. Chem. 1972, 37, 1003-1011.) Products were purified by flash chromatography on SiO$_2$ (particle size 0.032-0.063 mm). NMR spectra were obtained at 400 MHz ($^1$H NMR) and 100 MHz ($^{13}$C NMR) using CDCl$_3$ as solvent. Chemical shifts are reported in ppm relative to TMS. For CD analysis, samples were diluted to 5.0×10$^{-5}$ M with anhydrous chloroform and the instrument was purged with nitrogen for 20 minutes. Spectra were collected between 245 and 540 nm at 25.0° C. with a standard sensitivity of 100 mdeg, a data pitch of 0.5 nm, a band width of 1 nm, a scanning speed of 500 nm s$^{-1}$ and a response of 0.5 s using a quartz cuvette (1 cm path length). The data were adjusted by baseline correction and binomial smoothing.

1,8-Bis(2'-methyl-4'-methoxyphenyl)naphthalene (4)

A solution of 1,8-diiodonaphthalene, (1.70 g, 4.5 mmol), 2-methyl-4-methoxyphenylboronic acid, 2, (2.20 g, 13.4 mmol), Pd(PPh$_3$)$_4$ (0.78 g, 0.67 mmol) and K$_3$PO$_4$, (4.30 g, 20.1 mmol) in 50 mL toluene was stirred at 100° C. for 18 hours. The resulting mixture was allowed to come to room temperature, quenched with water and extracted with CH$_2$Cl$_2$. The combined organic layers were dried over MgSO$_4$ and concentrated in vacuo. Purification by flash chromatography on silica gel (CH$_2$Cl$_2$:hexanes 2:3) afforded 1.65 g (4.5 mmol, >99%) of off-white crystals containing syn- and anti-isomers of 7 in a ratio of 1:3.

$^1$H NMR: δ=1.76 (s, 4.6H), 1.83 (s, 1.4H), 3.69 (s, 4.4H), 3.71 (s, 1.4H), 6.28-6.39 (m, 4H), 6.66 (d, J=8.2 Hz, 0.5H), 6.87 (d, J=8.2 Hz, 1.5H), 7.16 (d, J=6.8 Hz, 2H), 7.46 (dd, J=7.2, 7.8 Hz, 2H), 7.89 (d, J=8.0, 2H). $^{13}$C NMR: δ=20.9, 21.0, 55.1, 55.2, 109.9, 110.3, 114.3, 114.4, 124.8, 125.0, 128.5, 129.0, 130.2, 130.4, 131.0, 131.6, 132.3, 134.8, 134.9, 135.2, 135.4, 136.5, 136.9, 139.5, 157.6, 158.1. Anal. Calcd. for C$_{26}$H$_{24}$O$_2$: C, 84.75; H, 6.57. Found: C, 84.74; H, 6.61.

1,8-Bis(2'-methyl-4'-methoxy-5'-formylphenyl)naphthalene (8)

Phosphorous oxychloride (2.9 mL, 31.2 mmol) and dimethyl formamide (2.4 mL, 31.2 mmol) were stirred in 10 mL of chloroform at room temperature for one hour. Then, 7 (0.60 g, 1.6 mmol) was added and the mixture was refluxed at 90° C. for 48 hours. It was then cooled to 0° C., carefully quenched with water and extracted with CH$_2$Cl$_2$. The combined organic layers were dried over MgSO$_4$ and concentrated in vacuo. Purification by flash chromatography on silica gel (CH$_2$Cl$_2$:EtOAc 25:1) afforded 0.69 g (1.6 mmol, 99%) of syn/anti-8 as a white powder. The diastereomers of 8 can be separated using flash chromatography with gradient elution starting with dichloromethane to collect the anti-isomer (73%), then increasing the polarity to DCM:EtOAc 15:1 to recover the syn-diastereomer (27%).

$^1$H NMR anti-8: δ=1.81 (s, 6H), 3.80 (s, 6H), 6.35 (s, 2H), 7.15 (d, J=7.0 Hz, 2H), 7.38 (s, 2H), 7.50 (dd, J=7.0, 8.2 Hz, 2H), 7.94 (d, J=8.2, 2H), 10.28 (s, 2H). $^{13}$C NMR: δ=21.5, 55.5, 112.1, 121.6, 125.2, 127.8, 129.2, 130.1, 130.2, 134.8, 135.4, 137.4, 146.2, 160.3, 189.0. $^1$H NMR syn-8: δ=1.90 (s, 6H), 3.85 (s, 6H), 6.42 (s, 2H), 7.14 (d, J=8.2 Hz, 2H), 7.15 (s, 2H), 7.49 (dd, J=7.0, 8.2 Hz, 2H), 7.94 (d, J=8.2, 2H), 10.17 (s, 2H). $^{13}$C NMR: δ=21.6, 55.6, 112.0, 122.0, 125.0, 129.0, 130.3, 131.3, 131.8, 135.2, 137.5, 144.1, 159.5, 188.7. Anal. Calcd. for C$_{28}$H$_{24}$O$_4$: C, 79.22; H, 5.70. Found: C, 78.99; H, 5.72.

1,8-Bis(2'-methyl-4'-hydroxy-5'-formylphenyl)naphthalene (5)

To a solution of 1,8-bis(2'-methyl-4'-methoxy-5'-formylphenyl)naphthalene, 8, (0.78 g, 1.9 mmol) in 35 mL of anhydrous $CH_2Cl_2$ at 0° C., $BBr_3$ (11.8 mL, 11.8 mmol) was added dropwise and the mixture was stirred for six hours. The reaction was carefully quenched with isopropyl alcohol followed by addition of water, and extracted with $CH_2Cl_2$. The combined organic layers were dried over $MgSO_4$ and concentrated in vacuo. Purification by flash chromatography on silica gel ($CH_2Cl_2$:hexanes 20:1) afforded 0.58 g of 5 (1.5 mmol, 77%) as a white solid. The anti/syn-ratio was determined as 20:1 by $^1$H-NMR spectroscopy. Enantiopure anti-5 was obtained via formation of 9 or 10 as described below and hydrolysis or by asymmetric transformation of the first kind and subsequent hydrolysis (see SI).

$^1$H NMR (P,P)-5: δ=1.85 (s, 6H), 6.40 (s, 2H), 7.08 (s, 2H), 7.20 (d, J=7.1 Hz, 2H), 7.54 (dd, J=7.0 Hz, 7.1 Hz, 2H), 7.99 (d, J=7.0 Hz, 2H), 9.66 (s, 2H), 10.73 (s, 2H). $^{13}$C NMR: δ=21.7, 117.5, 118.0, 125.3, 125.4, 129.4, 129.5, 130.6, 132.9, 135.0, 136.9, 146.5, 160.5, 195.1. Anal. Calcd. for $C_{26}H_{20}O_4$: C, 78.77; H, 5.09. Found: C, 78.69; H, 5.42.

Diimine (9)

To racemic 5 (67.0 mg, 0.17 mmol) dissolved in 8 mL of $CHCl_3$ over molecular sieves (4 Å, beads, 8-12 mesh), 2 equivalents of (R)-2-amino-1-propanol (25.4 mg, 0.34 mmol) were added and the mixture was allowed to stir for one hour at room temperature. The mixture was then extracted with water, dried over $MgSO_4$ and concentrated in vacuo. Chromatographic purification using EtOAc:EtOH (99.5:0.5) as mobile phase allowed the isolation of the two diastereomeric products (P,P,R,R)-9 and (M,M,R,R)-9 as yellow solids in quantitative yield.

$^1$H NMR (P,P,R,R)-9: δ=1.26 (d, J=6.4 Hz, 6H), 1.67 (s, 6H), 3.43 (t, J=6.4 Hz, 2H), 3.62 (m, 2H), 3.72 (dd, J=2.0 Hz, 12.0 Hz, 2H), 6.50 (s, 2H), 6.56 (s, 2H), 7.16 (d, J=7.0 Hz, 2H), 7.49 (dd, J=7.0 Hz, 8.0 Hz, 2H), 7.95 (m, 4H). $^{13}$C NMR: δ=17.8, 20.8, 66.8, 67.2, 114.9, 117.8, 125.1, 129.0, 129.8, 130.8, 131.2, 133.4, 134.8, 138.0, 141.9, 161.8, 164.3. Anal. Calcd. for $C_{32}H_{34}N_2O_4$: C, 75.27; H, 6.71; N, 5.49. Found: C, 75.05; H, 6.98; N, 5.14.

Hydrolysis of (P,P,R,R)-9 to (P,P)-5

Pure (P,P,R,R)-9 (43.2 mg, 0.08 mmol) was dissolved in 5 mL of 1 M NaOH, and 1 mL of aqueous HCl (12.1 M) was added dropwise at 0° C. The mixture was allowed to stir for 10 minutes. The resulting suspension was extracted with $CH_2Cl_2$ and the combined organic layers were dried over $MgSO_4$ and concentrated in vacuo. Purification by flash chromatography on silica gel ($CH_2Cl_2$) afforded enantiopure (P,P)-5 (28.5 mg, 0.07 mmol) in 85% yield, with no sign of the syn-diastereomer based on NMR analysis. The enantiopurity of 5 was confirmed by derivatization to the corresponding diimine using (R)-2-amino-1-propanol. The NMR spectrum of the condensation product showed the presence of a single diastereomer.

Diimine (P,P,R,R)-10

To racemic 5 (200 mg, 0.51 mmol) dissolved in 15 mL of $CHCl_3$ over molecular sieves (4 Å, beads, 8-12 mesh), 2 equivalents of (R)-2-amino-3-methyl-1-butanol (104 mg, 1.02 mmol) were added and the mixture was allowed to stir at 70° C. for 16 h. Upon completion of the asymmetric transformation, the mixture was cooled to room temperature, extracted with water, dried over $MgSO_4$, and concentrated in vacuo. Chromatographic purification using $CH_2Cl_2$:EtOAc (1:1) as mobile phase gave (P,P,R,R)-10 (285 mg, 0.50 mmol) in 99.8% yield.

$^1$H NMR (P,P,R,R)-10: δ=0.96 (d, J=6.8 Hz, 12H), 1.64 (s, 6H), 1.91 (m, 2H), 3.05 (m, 2H), 3.68 (t, J=10.5 Hz, 2H), 3.87 (m, 2H), 6.50 (s, 2H), 6.59 (s, 2H), 7.16 (d, J=7.0 Hz, 2H), 7.50 (dd, J=7.0 Hz, 8.0 Hz, 2H), 7.94 (m, 4H). $^{13}$C NMR: δ=18.6, 20.0, 20.8, 29.9, 64.2, 114.7, 118.1, 125.2, 128.9, 129.7, 130.9, 131.1, 133.2, 134.7, 138.1, 142.3, 163.0, 165.0. Anal. Calcd. for $C_{36}H_{42}N_2O_4$: C, 76.29; H, 7.47; N, 4.94. Found: C, 76.18; H, 7.28; N, 4.87.

The hydrolysis of (P,P,R,R)-10 to (P,P)-5 was conducted as described above with (P,P,R,R)-9 and gave enantiopure (P,P)-5 in 80% yield.

1. Deracemization of 5 Via Asymmetric Transformation of the First Kind with 9

Racemic 5 (10.14 mg, 0.026 mmol) was dissolved in 1.0 mL of $CDCl_3$. Molecular sieves (4 Å, beads, 8-12 mesh) were added and the mixture was stirred with 2 equivalents of (R)-2-amino-1-propanol (3.84 mg, 0.051 mmol) for one hour at 25° C. After the diimine formation was complete, $^1$H NMR analysis indicated the presence of two diastereomers—evidenced for example by the two doublets at 1.26 and 1.40 ppm. (FIG. 1). Upon heating to 58.0° C., the signals of the thermodynamically less favored diastereomer decreased in intensity. In agreement with the amplification of asymmetric induction observed upon diimine formation of 1,8-bis(3'-formyl-4'-hydroxyphenyl)naphthalene with (R)-2-amino-1-propanol, it is assumed that the central chirality of amino alcohol controls the stereoselective outcome of this atropisomerization process. The mixture is almost entirely converted to the more stable diastereomer after 14 hours (FIG. 1).

Pure (P,P,R,R)-9 (43.2 mg, 0.08 mmol) was dissolved in 5 mL of 1 M NaOH, and 1 mL of aqueous HCl (12.1 M) was added dropwise at 0° C. The mixture was allowed to stir for 10 minutes. The resulting suspension was extracted with $CH_2Cl_2$ and the combined organic layers were dried over $MgSO_4$ and concentrated in vacuo. Purification by flash chromatography on silica gel ($CH_2Cl_2$) afforded enantiopure (P,P)-5 (28.5 mg, 0.07 mmol) in 85% yield, with no sign of the syn-diastereomer based on NMR analysis. The enantiopurity of 5 was confirmed by derivatization to the corresponding diimine using (R)-2-amino-1-propanol. The NMR spectrum of the condensation product showed the presence of a single diastereomer.

2. Deracemization of 5 Via Asymmetric Transformation of the First Kind with 10

Figure 9:
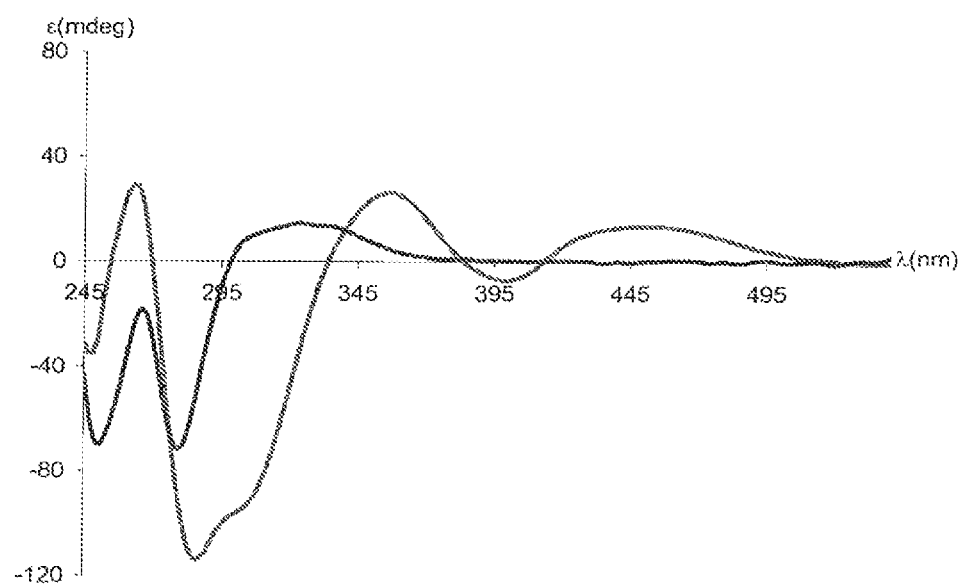
FIG. 9 depicts a CD spectra of (P,P)-5 (blue), (P,P,R,R)-10 (red) at $5.0 \times 10^{-5}$ M in CHCl$_3$.

The diimine (P,P,R,R)-10 was prepared in quantitative yields from racemic 5 and (R)-2-amino-3-methyl-1-butanol using the same asymmetric transformation protocol as described above for 9. The hydrolysis of (P,P,R,R)-10 to (P,P)-5 was conducted as described above with (P,P,R,R)-9 and gave enantiopure (P,P)-5 in 80% yield. The CD spectra of (P,P,R,R)-10 and (P,P)-5 are shown in FIG. 9.

Figure 10:
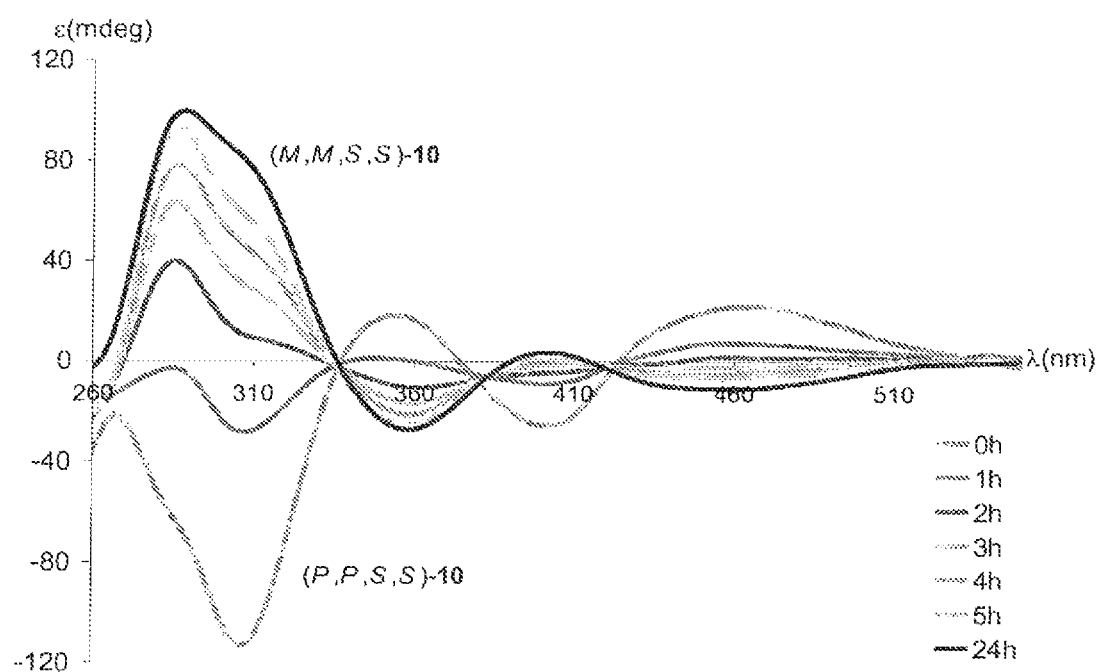
FIG. 10 depicts the change in the CD signal of (P,P,S,S)-10 as a result of diastereomerization at 50.0° C. The CD spectra were collected at 25.0° C. with a concentration of $5.0 \times 10^{-5}$ M in CHCl$_3$.

The unidirectional atropisomerization of (P,P,S,S)-10 to (M,M,S,S)-10 was monitored by CD spectroscopy and is in perfect agreement with the results obtained with 9. Enantiopure (P,P)-5 (10.14 mg, 0.026 mmol) was dissolved in 1.0 mL of $CDCl_3$. Molecular sieves (4 Å, beads, 8-12 mesh) were added and the mixture was stirred with 2 equivalents of (S)-2-amino-3-methyl-1-butanol (5.52 mg, 0.051 mmol) for one hour at 25.0° C. The mixture was then heated to 50.0° C. Aliquots were taken at one hour intervals and diluted to 5.0×10⁻⁵ M with anhydrous CHCl₃ for CD analysis. After 24 hours, the CD signal indicated almost complete diasteriomerization (FIG. 10).

3. Determination of the Initial Rate Constant for the Isomerization of (P,P,S,S)-9

Figure 11:
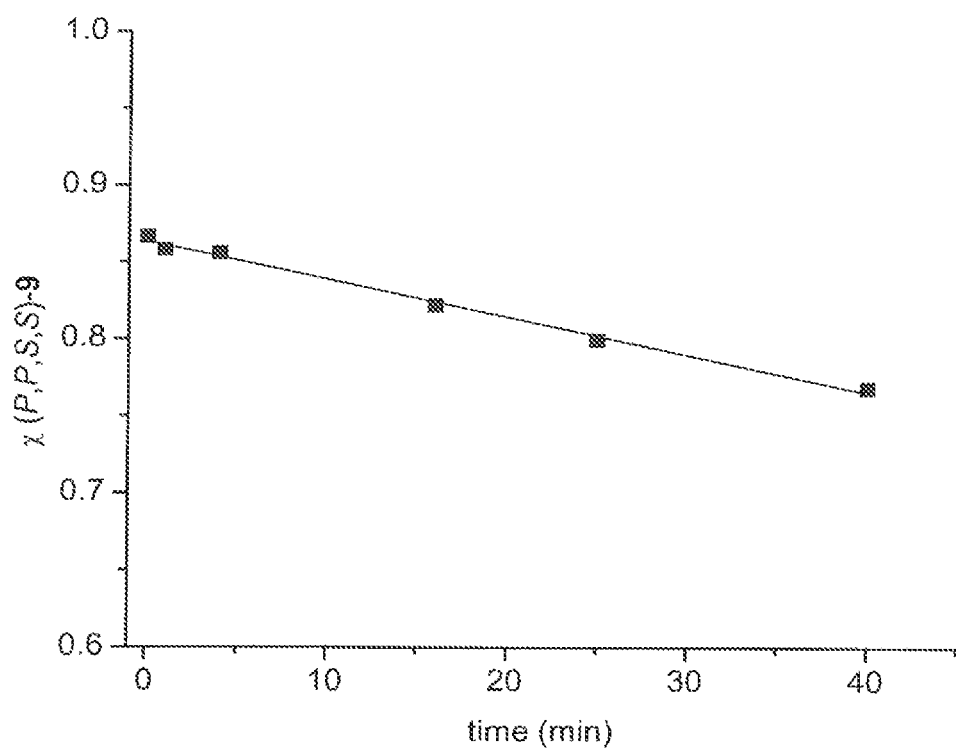
FIG. 11 depicts a plot of the mol fraction of (P,P,S,S)-9 versus time (min).

Enantiopure (P,P)-5 (10.14 mg, 0.026 mmol) was dissolved in 1.0 mL of CDCl₃. Molecular sieves (4 Å, beads, 8-12 mesh) were added and the mixture was stirred with 2 equivalents of (S)-2-amino-1-propanol (3.84 mg, 0.051 mmol) for one hour at 25° C. The mixture was then heated to 58.0° C. and $^1$H-NMR spectra were collected at short intervals to follow the decay of (P,P,S,S)-9 (same signals as (M,M,R,R)-9, FIG. 1) before the appearance of any (M,M,S,S)-9 (same signals as (P,P,R,R)-9, FIG. 1). By plotting the mol fraction of (P,P,S,S)-9 versus time, the initial rate of the reaction can be obtained from the slope of the fitted line (FIG. 11). Curve fitting to y=A1x+B was performed using OriginPro 8.1, with A1=−0.00245 and B=0.8634, A2=0.351, with $R^2$=0.9929. The initial rate constant denoted $k_1$ was determined as 4.083×10⁻⁵ s⁻¹, $\Delta G^{\neq}_{(P,P,S,S)\text{-}9 \rightarrow (P,M,S,S)\text{-}9}$=109.2 kJ/mol.

4. Determination of the Rate Constants for the Isomerization of 9²⁰

As described above, enantiopure (P,P)-5 (10.12 mg, 0.026 mmol) was dissolved in 1.0 mL of CDCl₃, treated with 2 equivalents of (S)-2-amino-1-propanol (3.84 mg, 0.051 mmol) for one hour at 25° C., and then heated to 58.0° C. $^1$H-NMR spectra were collected at different intervals to monitor the change in the intensity of the resolved methyl signals of (P,P,S,S)-9 (1.69 ppm), (M,P,S,S)-9 (1.81 ppm) and (M,M,S,S)-9 (1.66 ppm) until equilibrium was reached.

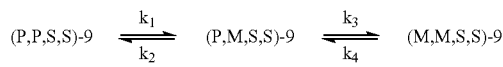

The relative amounts of the three stereoisomers at equilibrium were determined as 94.4:3.9:1.7 [(M,M,S,S):(P,P,S,S):(M,P,S,S)] in CDCl₃ at 58.0° C. The individual rate constants were then calculated as described in the SI.

5. Kinetic Resolution

Scheme 8. Kinetic resolution of 2-amino-1-propanol using (P,P)-5

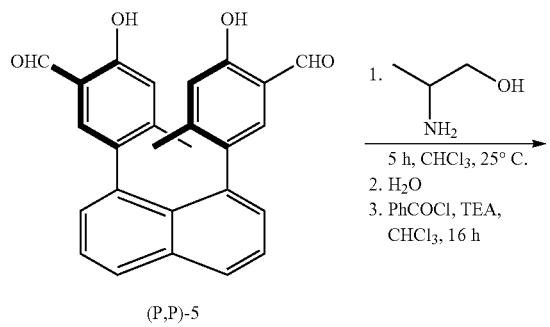

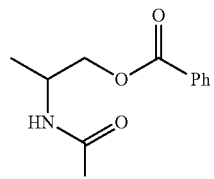

11

Enantiopure (P,P)-5 (15.89 mg, 0.040 mmol) was dissolved in 1.0 mL of anhydrous CHCl₃. Molecular sieves (4 Å, beads, 8-12 mesh) were added and the mixture was stirred with 4 equivalents of racemic 2-amino-1-propanol (12.04 mg, 0.160 mmol) for 5 hours at 25° C. The mixture was then extracted with water, and the aqueous layer was freeze-dried to recover the unreacted amino alcohol. The crude material (6.02 mg, 0.080 mmol) was dissolved in 1.5 mL of chloroform and treated with benzoyl chloride (117.8 mg, 0.801 mmol) in the presence of triethylamine (162.2 mg, 1.60 mmol). The mixture was allowed to stir for 16 hours, then quenched with water, and extracted with CH₂Cl₂. The combined organic layers were dried over MgSO₄ and concentrated in vacuo. Purification by flash chromatography on silica gel (CH₂Cl₂:EtOAc 9:1) afforded 11 (22.0 mg, 0.074 mmol) as a colorless oil in 93%. The ee was determined as 54% by HPLC on Chiralpak AD using hexanes:ethanol (90:10) as mobile phase. As expected, formation of (P,P,R,R)-9 is favored and comparison of the HPLC chromatogram with separately prepared enantiopure samples of 11 proved that 77% of the unreacted amino alcohol had (S)-configuration.

6. Crystallization and X-Ray Diffraction

Single crystal X-ray analysis was performed at 100 K using a Siemens platform diffractometer with graphite monochromated Mo—Kα radiation (λ=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameters.

A crystal of enantiopure (P,P)-5 was obtained by slow evaporation of a solution of 5.0 mg of (P,P)-5 in 3 mL of CHCl₃. Crystal structure data for (P,P)-5: Formula C₂₆H₂₀O₄, M=396.43, crystal dimensions 0.15×0.10×0.05 mm, tetragonal, space group P4₃, a=11.7955(17) Å, b=11.7955 (17) Å, c=28.4769(40) Å, V=3962.10 Å³, Z=1, $\rho_{calcd}$=1.3290 g cm⁻³.

Selected Distances and Angles:

| | |
|---|---|
| Phenyl-phenyl [Å] (entroids to entroids) | 3.470 |
| Splaying angle between salicylidenimine planes [°] | 20.51 |
| Torsion angle [°] | 5.32 |

The slow evaporation of a solution of 5.0 mg of 5 and 2 equivalents of (R)-2-amino-1-propanol in 3 mL of CHCl₄ afforded single crystals of syn-9. Crystal structure data for syn-9: Formula C₃₂H₃₄N₂O₄, M=510.62, crystal dimensions 0.120×0.10×0.07 mm, monoclinic, space group P2₁/c, a=22.3400(21) Å, b=6.8469 (6) Å, c=17.6753 (16) Å, β=100.956 (1), V=2654.33 Å³, Z=4, $\rho_{calcd}$=1.2726 g cm³.

33

Selected Distances and Angles:

| | |
|---|---|
| Phenyl-phenyl [Å] (entroids to entroids) | 3.518 |
| Splaying angle between salicylidenimine planes [°] | 21.09 |
| Torsion angle [°] | 18.33 |

A crystal of (P,P,R,R)-10 was obtained by crystallization of 100.0 mg of (P,P,R,R)-10 from 15 mL of hexanes. Crystal structure data for (P,P,R,R)-10: Formula $C_{32}H_{34}N_2O_4$, M=−566.73, crystal dimensions 0.10×0.10×0.05 mm, orthorhombic, space group $P2_1$, a=10.8469(44) Å, b=21.3655 (86) Å, c=13.6440 (55) Å, V=3161.99 Å$^3$, Z=2, $\rho_{calcd}$=1.1903 g cm$^4$.

Selected Distances and Angles:

| | |
|---|---|
| C═N ... HOC$_{phenyl}$ hydrogen bond length [Å] | 1.861 |
| C$_{aliph}$OH ... OC$_{phenyl}$ hydrogen bond length [Å] | 2.178 |
| Phenyl-phenyl [Å] (entroids to entroids) | 3.326 |
| Splaying angle between salicylidenimine planes [°] | 13.46 |
| Torsion angle [°] | 18.17 |

B. Experimental Procedures for Synthesizing 2

All reagents and solvents were used without further purification. All reactions were carried out under nitrogen atmosphere and anhydrous conditions. Products were purified by flash chromatography on SiO$_2$ (particle size 0.032-0.063 mm). NMR spectra were obtained at 400 MHz ($^1$H NMR) and 100 MHz ($^{13}$C NMR) using CDCl$_3$ as solvent. Chemical shifts are reported in ppm relative to TMS.

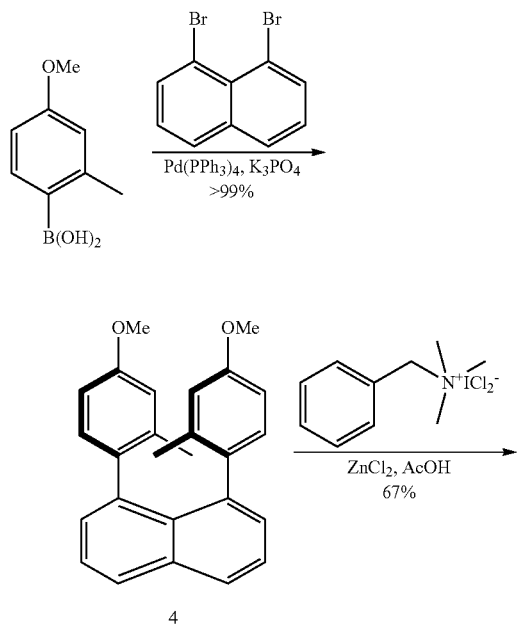

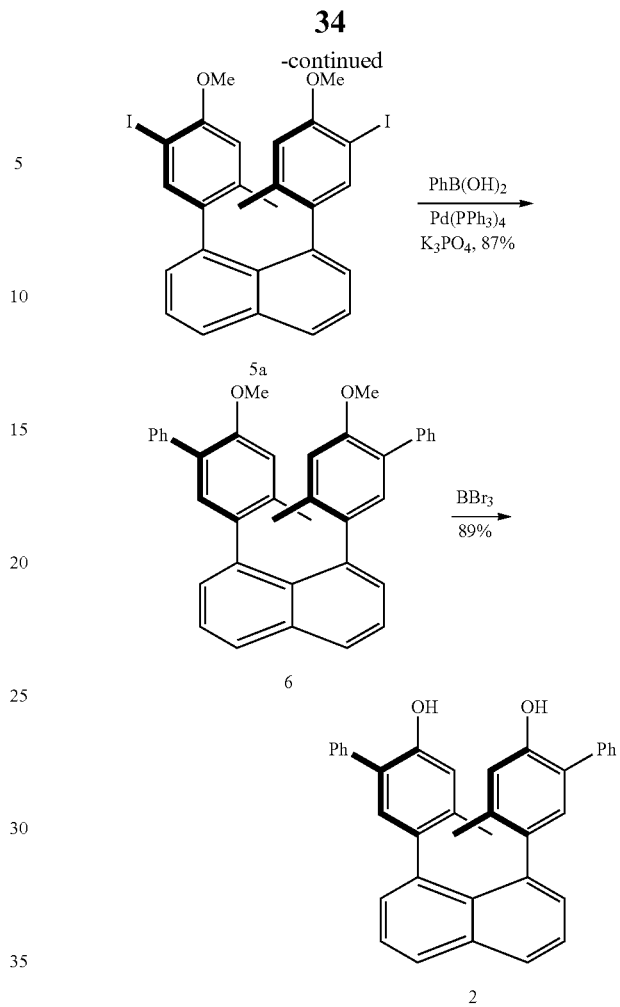

1,8-Bis(2'-methyl-4'-methoxyphenyl)naphthalene (4)

A solution of 1,8-dibromonaphthalene, (1.29 g, 4.5 mmol), 2-methyl-4-methoxyphenylboronic acid, 3, (2.24 g, 13.5 mmol), Pd(PPh$_3$)$_4$ (0.78 g, 0.68 mmol) and K$_3$PO$_4$, (4.30 g, 20.0 mmol) in 50 mL toluene was stirred at 110° C. for 18 hours. The resulting mixture was allowed to come to room temperature, quenched with water and extracted with CH$_2$Cl$_2$. The combined organic layers were dried over MgSO$_4$ and concentrated in vacuo. Purification by flash chromatography on silica gel (CH$_2$Cl$_2$:hexanes 2:3) afforded 1.66 g (4.5 mmol, >99%) of off-white crystals containing syn- and anti-isomers of 4.

$^1$H NMR: δ=1.76 (s, 4.6H), 1.83 (s, 1.4H), 3.69 (s, 4.4H), 3.71 (s, 1.4H), 6.28-6.39 (m, 4H), 6.66 (d, J=8.2 Hz, 0.5H), 6.87 (d, J=8.2 Hz, 1.5H), 7.16 (d, J=6.8 Hz, 2H), 7.46 (dd, J=6.8 Hz, 8.0 Hz, 2H), 7.89 (d, J=8.0 Hz, 2H). $^{13}$C NMR: δ=20.9, 21.0, 55.1, 55.2, 109.9, 110.3, 114.3, 114.4, 124.8, 125.0, 128.5, 129.0, 130.2, 130.4, 131.0, 131.6, 132.3, 134.8, 134.9, 135.2, 135.4, 136.5, 136.9, 139.5, 157.6, 158.1. Anal. Calcd. for C$_{26}$H$_{24}$O$_2$: C, 84.75; H, 6.57. Found: C, 84.74; H, 6.61.

1,8-Bis(2'-methyl-4'-methoxy-5'-iodophenyl)naphthalene (5$^a$)

To a solution of 4 (0.18 g, 0.49 mmol) in 8 mL, of acetic acid, benzyltrimethylammonium dichloroiodate (0.38 g, 1.08 mmol) and zinc dichloride (0.15 g, 1.08 mmol) dissolved in 8 mL of acetic acid were added dropwise over 30 minutes, and the mixture was stirred at 55° C. for 20 hours. It was then cooled to 0° C., carefully quenched with water and extracted with $CH_2Cl_2$. The combined organic layers were washed with 1 M sodium thiosulfate, dried over $MgSO_4$ and concentrated in vacuo. Purification by flash chromatography on silica gel (hexanes:$CH_2Cl_2$ 3:1) afforded 0.20 g (0.33 mmol, 67%) of 5a as a white solid.

$^1H$ NMR: δ=1.86 (s, 6H), 3.83 (s, 6H), 6.41 (s, 2H), 7.15 (d, J=6.9 Hz, 2H), 7.27 (s, 2H), 7.48 (dd, J=6.9 Hz, 8.1 Hz, 2H), 7.92 (d, J=8.11 Hz, 2H). $^{13}C$ NMR: δ=20.7, 56.2, 82.0, 111.2, 125.0, 129.0, 130.2, 134.9, 136.8, 137.5, 137.6, 138.3, 156.2. Anal. Calcd. for $C_{26}H_{22}I_2O_2$: C, 50.35; H, 3.58. Found: C, 50.15; H, 3.52.

1,8-Bis(6'-methoxy-4'-methylbiphenyl-3'-yl)naphthalene (6)

A solution of 5a (0.20 g, 0.32 mmol), phenylboronic acid (0.12 g, 0.96 mmol), $Pd(PPh_3)_4$ (0.055 g, 0.048 mmol) and $K_3PO_4$, (0.31 g, 1.44 mmol) in 5 mL of toluene was stirred at 110° C. for 18 hours. The resulting mixture was allowed to come to room temperature, quenched with water and extracted with $CH_2Cl_2$. The combined organic layers were dried over $MgSO_4$ and concentrated in vacuo. Purification by flash chromatography on silica gel ($CH_2Cl_2$:hexanes 1:2) afforded 0.14 g (0.28 mmol, 87%) of 6 as a white solid.

$^1H$ NMR: δ=1.70 (s, 6H), 3.67 (s, 6H), 6.36 (s, 2H), 7.00 (s, 2H), 7.21-7.31 (m, 6H), 7.38 (dd, J=7.5 Hz, 7.7 Hz, 4H), 7.45-7.52 (m, 6H), 7.92 (d, J=8.2 Hz, 2H). $^{13}C$ NMR: δ=20.7, 55.5, 125.1, 126.3, 126.5, 127.9, 128.6, 129.2, 130.2, 130.6, 130.9, 134.8, 135.3, 136.4, 138.6, 139.1, 154.7. Anal. Calcd. for $C_{38}H_{32}O_2$: C, 87.66; H, 6.19. Found: C, 87.42; H, 6.47.

1,8-Bis(6'-hydroxy-4'-methylbiphenyl-3'-yl)naphthalene (2)

To a solution of 1,8-bis(2'-methyl-4'-methoxy-5'-phenylphenyl)naphthalene, 6, (0.14 g, 0.28 mmol) in 10 mL of anhydrous $CH_2Cl_2$ at 0° C., $BBr_3$ (1.67 mL, 1.67 mmol) was added dropwise and the mixture was stirred for sixteen hours at room temperature. The reaction was carefully quenched with isopropyl alcohol followed by addition of water, and extracted with $CH_2Cl_2$. The combined organic layers were dried over $MgSO_4$ and concentrated in vacuo. Purification by flash chromatography on silica gel ($CH_2Cl_2$) afforded 0.12 g of 2 (0.25 mmol, 89%) as a white solid.

$^1H$ NMR: δ=1.66 (s, 6H), 5.01 (s, 2H), 6.45 (s, 2H), 6.89 (s, 2H), 7.25 (d, J=7.0 Hz, 2H), 7.36 (dd, J=6.8 Hz, 7.2 Hz, 2H), 7.42-7.51 (m, 10H), 7.91 (d, J=8.1 Hz, 2H). $^{13}C$ NMR: δ=20.3, 115.9, 124.2, 125.0, 127.5, 128.6, 128.8, 129.2, 129.9, 130.3, 130.9, 150.7. Anal. Calcd. for $C_{36}H_{28}O_2$: C, 87.78; t, 5.73. Found: C, 88.04; H, 5.79.

1,8-Bis(6'-N-Boc-L-tryptophan-4'-methylbiphenyl-3'-yl)naphthalene (7)

A solution of 6 (0.17 g, 0.35 mmol), N-Boc-L-tryptophan (0.24 g, 0.77 mmol), N,N'-dicyclohexylcarbodiimide (0.17 g, 0.81 mmol) and DMAP (0.05 g, 0.42 mmol) was stirred in 5 mL of dichloromethane for 16 hours at room temperature. The resulting suspension was dried and subjected to gradient flash chromatography on silica gel (dichloromethane:ethyl acetate 70:1 to 60:1) to afford 0.18 g (0.17 mmol, 49%) and 0.16 g (0.15 mmol, 42%) of the first and second eluting diastereomers of 7 as white solids.

$^1H$ NMR (first eluting): δ=1.38 (s, 6H), 1.43 (s, 18H), 3.22 (m, 4H), 4.26 (m, 1H), 5.01 (m, 1H), 5.63 (s, 2H), 6.79 (s, 2H), 6.97-7.28 (m, 26H), 7.94 (d, J=8.1 Hz, 2H), 9.33 (s, 2H). $^{13}C$ NMR: δ=20.1, 28.3, 54.5, 80.0, 109.8, 111.3, 118.7, 119.5, 121.9, 122.0, 123.3, 124.9, 127.0, 127.7, 128.4, 128.7, 121.9, 123.3, 124.9, 127.0, 127.7, 128.7, 129.8, 131.2, 136.2, 137.3, 138.1, 140.5, 145.5, 155.2, 170.9. Anal. Calcd. for $C_{68}H_{64}N_4O_8$: C, 76.67; H, 6.06; N, 5.26. Found: C, 76.44; H, 6.16; N, 5.62.

$^1H$ NMR (second eluting): δ=1.40 (s, 18H), 1.70 (s, 6H), 3.12 (m, 4H), 4.82 (m, 1H), 5.02 (m, 1H), 6.65 (s, 2H), 6.88 (s, 2H), 7.11-7.31 (m, 18H), 7.51 (m, 2H), 7.92 (d, J=8.2 Hz, 2H), 8.41 (s, 2H). $^{13}C$ NMR: δ=20.1, 28.3, 54.5, 80.0, 109.8, 111.1, 118.7, 119.5, 122.0, 122.9, 123.1, 124.9, 127.3, 127.9, 128.2, 128.8, 130.3, 131.5, 135.2, 136.0, 136.1, 137.2, 138.1, 140.51, 145.7, 155.46, 170.4. Anal. Calcd. for $C_{68}H_{64}N_4O_8$: C, 76.67; H, 6.06; N, 5.26. Found: C, 76.43; H, 6.27; N, 5.42.

1,8-Bis(6'-hydroxy-4'-methylbiphenyl-3'-yl)naphthalene (2)

A suspension of the first eluting diastereomer of 7 (0.04 g, 0.038 mmol) in 3.8 M KOH (10 mL, 4:1 ethanol:water) was stirred for 3 hours at room temperature. The resulting mixture was quenched with 0.5 mL of concentrated HCl at 0° C. It was then extracted with dichloromethane, and the combined organic layers were washed with brine, dried over $MgSO_4$ and concentrated in vacuo. The crude was then subjected to gradient flash chromatography on silica gel (dichloromethane) to afford 0.019 g (0.038 mmol, 99%) of enantiopure levorotatory-2 as a white solid. The same procedure was used to obtain dextrorotatory-2 by hydrolyzing the second eluting diastereomer of 7.

$^1H$ NMR: δ=1.66 (s, 6H), 5.01 (s, 2H), 6.45 (s, 2H), 6.89 (s, 2H), 7.25 (d, J=7.0 Hz, 2H), 7.36 (dd, J=6.8 Hz, 7.2 Hz, 2H), 7.42-7.51 (m, 10H), 7.91 (d, J=8.1 Hz, 2H). $^{13}C$ NMR: δ=20.3, 115.9, 124.2, 125.0, 127.5, 128.6, 128.8, 129.2, 129.9, 130.3, 130.9, 150.7. Anal. Calcd. for $C_{36}H_{28}O_2$: C, 87.78; t, 5.73. Found: C, 88.04; H, 5.79.

1. Resolution of 2

Figure 12:
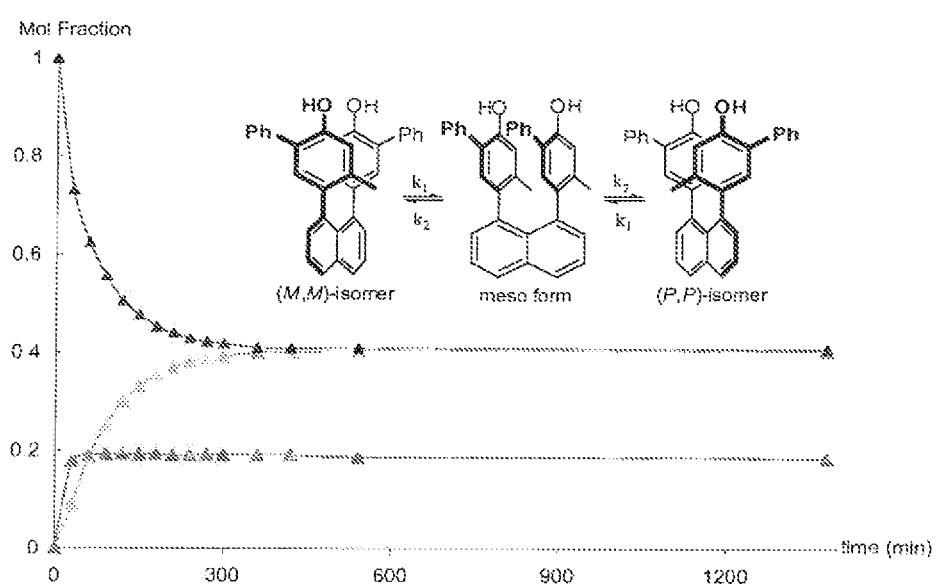
FIG. 12 depicts the change in the mol fractions of (−)-2 (blue), (+)-2 (orange) and syn-2 (green) during heating at 77.1° C.

We found that the enantiomers and the meso syn-isomer of 2 can be resolved by HPLC on Chiralpak AD or other means (see SI). Preparative isolation of the levorotatory enantiomer enabled us to monitor the racemization kinetics at 77.1° C. by chiral HPLC separation of cooled aliquots (FIG. 12). The syn/anti-ratio of 2 at equilibrium was determined as 0.46 and the reversible first order reaction kinetics were simulated and analyzed according to Vriens. (Vriens, G. N. *Ind. Eng. Chem.* 1954, 669-671.) The energy barrier to conversion of the trans-isomer to the syn-intermediate, $\Delta G^{\neq}_{anti \to syn}$, was determined as 110.0 kJ/mol. As expected, the Gibbs activation energy for the reversed process, $\Delta G^{\neq}_{syn \to anti}$, is slightly lower and was calculated as 107.7 kJ/mol (see SI).

Figure 13:
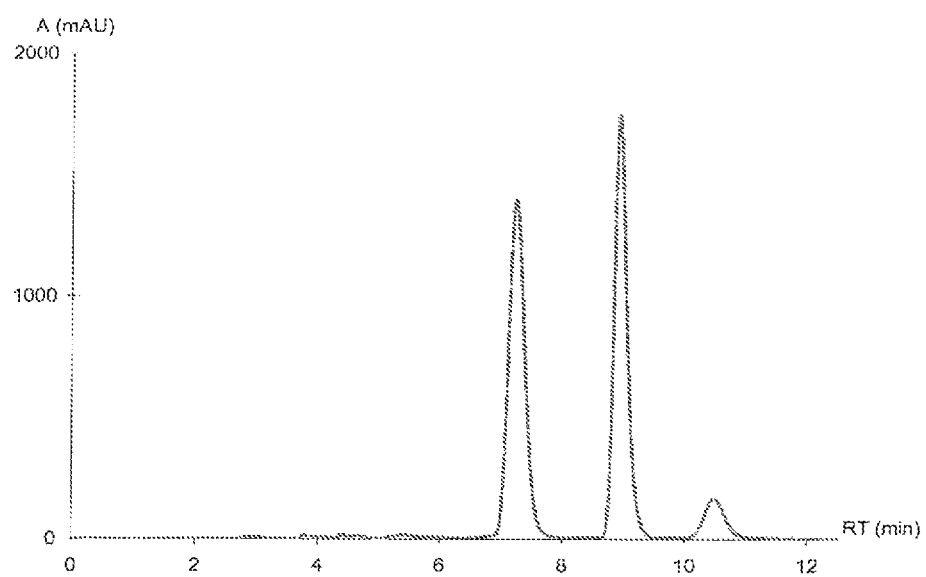
FIG. 13 depicts of a HPLC chromatogram of racemic 2.

The stereoisomers of 2 are separable on a CHIRALPAK AD column using hexanes:isopropyl alcohol (9:1) as mobile phase (FIG. 13). The first eluting enantiomer elutes at 7.2 min, while the second elutes at 8.9 min. The syn-intermediate elutes last at 10.5 min. The absorption coefficient of the syn-diastereomer was determined as 1124216.92 unit area/μmol, while that for the anti-isomer was 1607421.75 unit area/μmol.

To avoid this tedious separation process, several chiral auxiliaries were examined to allow for the large scale separation of enantiomers of 2 through the formation of entroidserie complexes. After screening several chiral auxiliaries, N-Boc-L-tryptophan was used to esterify racemic 2, and was followed by the chromatographic separation of the resulting diastereomers (Scheme 2). Finally, the diastereomers were hydrolyzed to regenerate the free phenols in their enantiomerically pure forms.

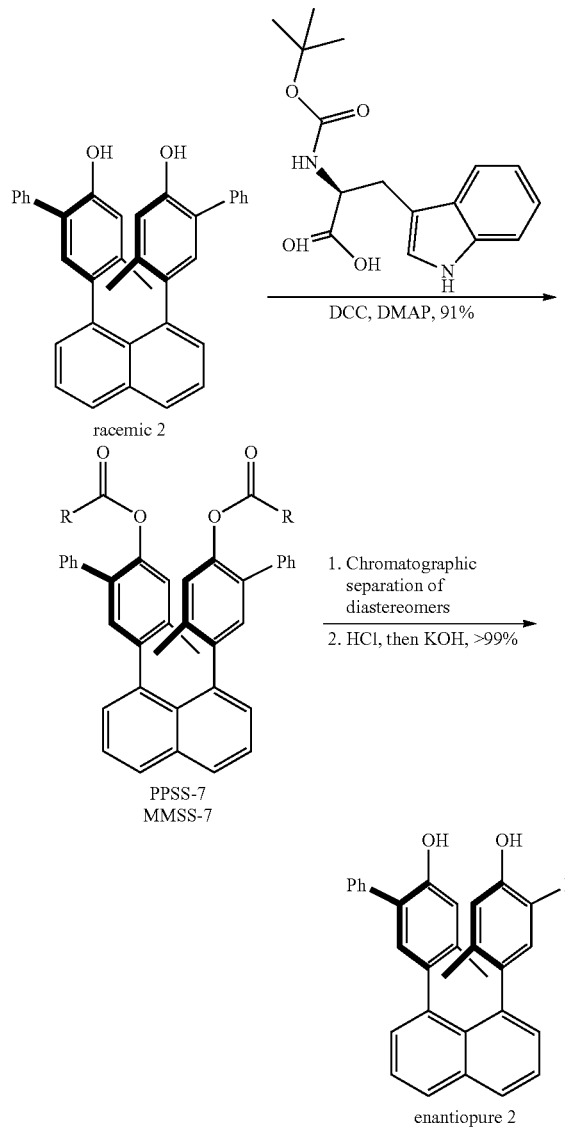

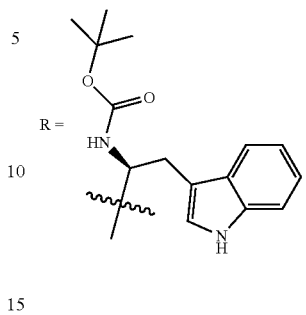

2. UV, CD and Polarimetry

Figure 14A:
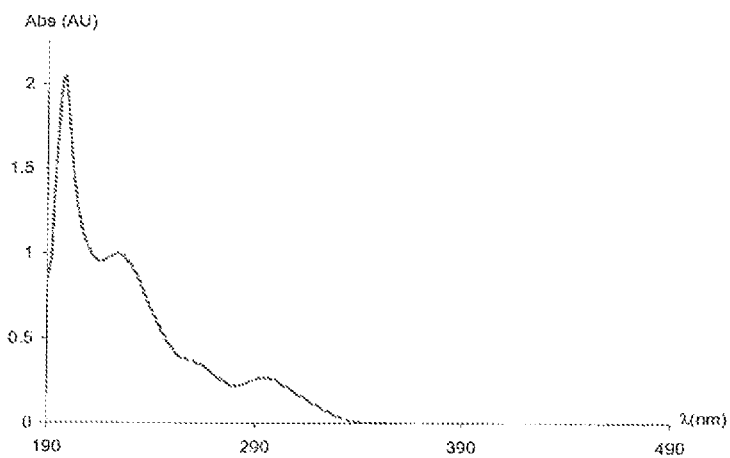
FIG. 14a depicts a UV spectrum of 2 ($1.02 \times 10^{-3}$ M, hexanes:IPA 1:1).
Figure 14B:
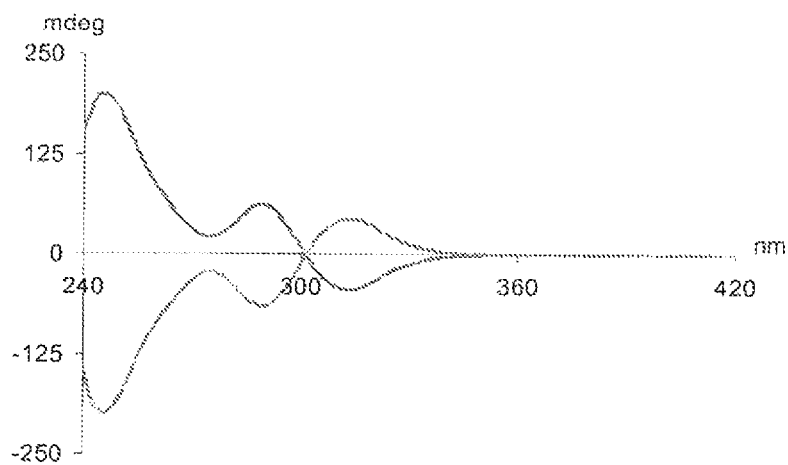
FIG. 14b depicts a CD spectra of dextrorotatory (blue) and levorotatory (orange) enantiomers of 2 ($9.45 \times 10^{-5}$ M, ACN).
Figure 15:
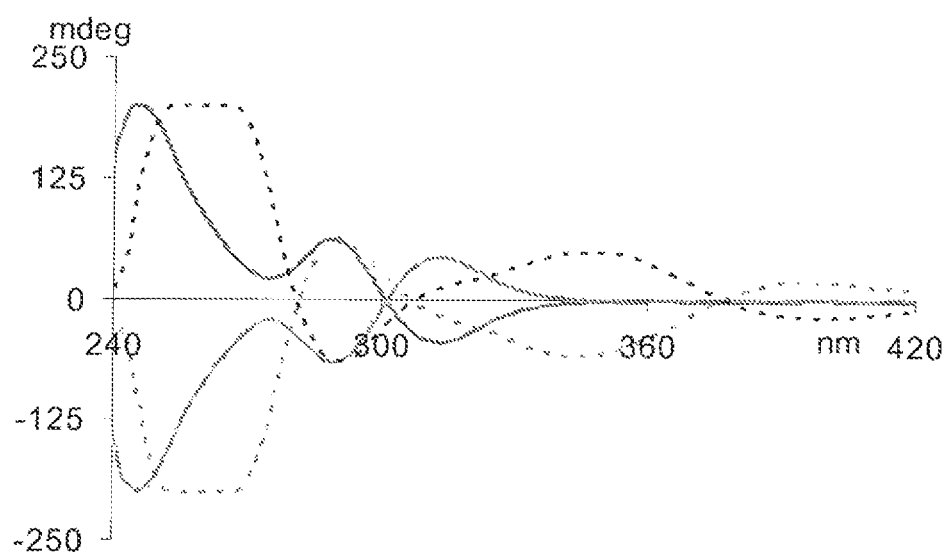
FIG. 15 depicts CD Spectra of dextrorotatory (blue) and levorotatory (orange) enantiomers of 2 ($9.45 \times 10^{-5}$ M, ACN). The dashed lines show the CD spectra upon treatment with sodium tert-butoxide.

The CD instrument was purged with nitrogen for 20 minutes. Spectra were collected at room temperature between 270 and 390 nm with a standard sensitivity of 100 mdeg, a data pitch of 0.5 nm, a band width of 1 nm, a scanning speed of 500 nm s$^{-1}$ and a response of 0.5 s using a quartz cuvette (1 cm path length). Polarimetric measurements at 21.5° C. allowed for the determination of the specific rotation $[\alpha]_D$ as 354 for the first eluting enantiomer, and −355 for the second. The CD spectra of the enantiomers of 2 are shown in FIG. 14. The effects on the CD spectra of the enantiomers of 2 upon treatment of sodium ter-butoxide is shown in FIG. 15.

3. Kinetic Studies

3.1. Isomerization Experiment

Figure 16:
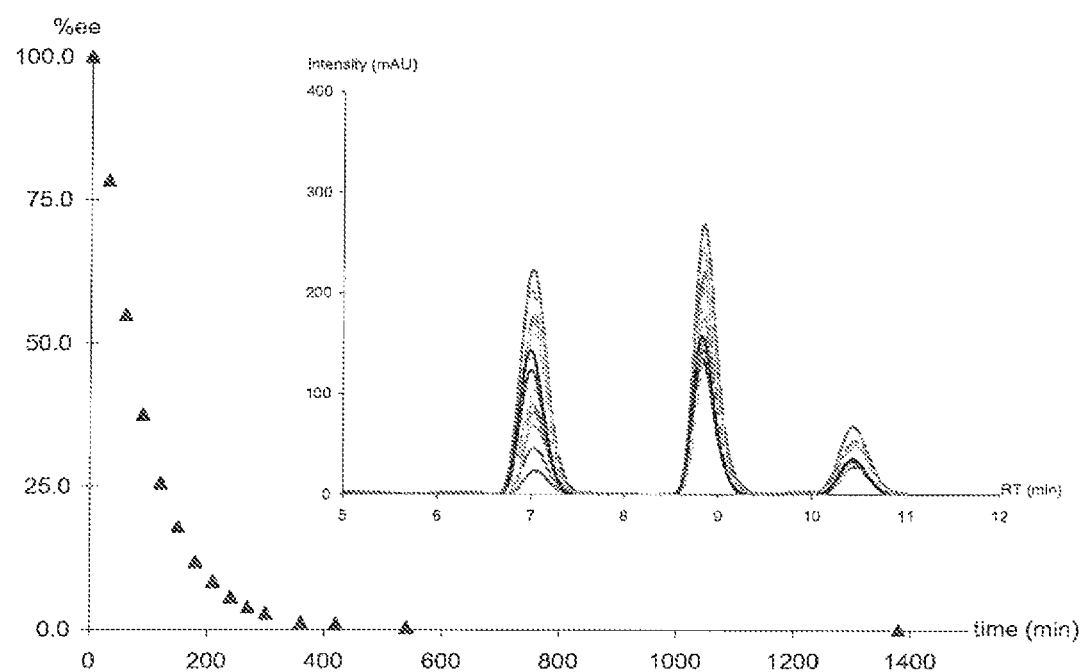
FIG. 16 depicts the change of the % ee of 2 during heating at 77.1° C. Inset: HPLC chromatograms showing the change in the relative amounts of the stereoisomers of 2.

Several solutions of the levorotatory enantiomer of 1 (1.02×10$^{-3}$ M, isopropyl alcohol) were prepared in separate vials and stirred at 77.1° C. (±0.4° C.). The temperature was continuously monitored using a calibrated digital thermometer. At various times, the stereoisomeric composition was determined using a rapidly cooled vial. From this vial, 50 μL were diluted with 1 mL of hexanes:IPA (9:1), and then analyzed by HPLC on CHIRALPAK AD and UV detection at 240 nm. (see FIG. 16)

3.2. Determination of the Rate Constants for the Isomerization of 2

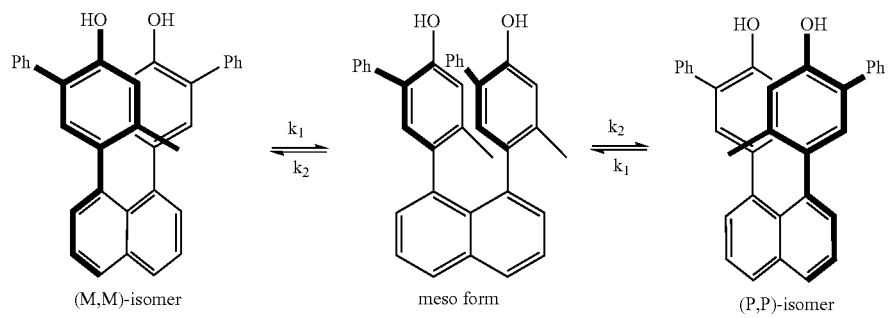

$$x = C_1 e^{D_1 k_1 t} + C_2 e^{D_2 k_1 t} + \frac{\alpha}{K_1 K_2 E_2} \quad (1)$$

Figure 17:
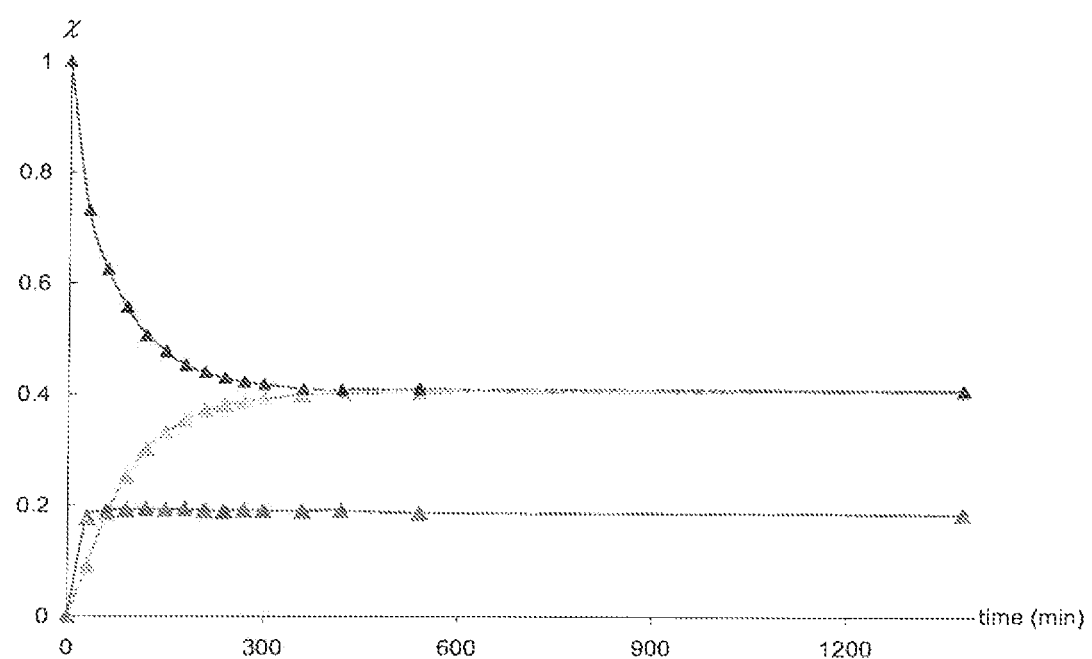
FIG. 17 depicts the change in the mol fractions of (−)-2 (blue), (+)-2 (orange) and syn-2 (green) during heating at 77.1° C.

$k_1$=rate constant for anti- to syn-interconversion
$k_2$=rate constant for syn- to anti-interconversion
$K_1$=equilibrium constant for the formation of the syn-isomer
$K_2$=equilibrium constant for the formation of the anti-isomer
$\alpha$=ratio of forward rate constants for the consecutive reactions FIG. 17 shows the decrease of the mol fraction of (−)-2 as a function of time. The mathematical solution for the kinetics of consecutive, first-order, reversible reactions involving 3 species such as the syn/anti-interconversion of 2 has been reported by Vriens.[7] Curve fit analysis using equation 2 allows for the determination of the rate constant for the anti- to syn-isomerization, $k_1$.

$$x = C_1 e^{D_1 k_1 t} + C_2 e^{D_2 k_1 t} + \frac{\alpha}{K_1 K_2 E_2} \quad (2)$$

$k_1$=rate constant of the anti- to syn-interconversion, $K_1$=equilibrium constant for the formation of the syn-isomer, $K_2$=equilibrium constant for the formation of either anti-isomer, $\alpha$=ratio of forward rate constants ($k_2/k_1$) for the consecutive, reversible, first-order reactions, $k_2$=rate constant for syn- to anti-interconversion, $C_1$, $C_2$, $D_1$, $D_2$, $E_2$ are constants. Curve fitting of the decay of (−)-2 to y=A1*exp (−x/t1)+ A2*exp(−x/t2)+y0 was performed using OriginPro 8.1, with A1=0.40745, A2=0.11968, t1=77.31456, t2=8.33489, y0=0.40745, $R^2$=0.9999.

The syn/anti-ratio of 2 at equilibrium was determined as 0.46. The mixture consists of 81.4% of racemic anti-2 and 19.1% of syn-2.

$$E_1 = 1 + \frac{1}{K_1} + \alpha + \frac{\alpha}{K_2} \quad E_2 = \alpha\left(1 + \frac{1}{K_1 K_2} + \frac{1}{K_2}\right) = D_1 D_2$$

$$D_1 = \frac{-E_1 + \sqrt{E_1^2 - 4E_2}}{2} \quad D_2 = \frac{-E_1 - \sqrt{E_1^2 - 4E_2}}{2}$$

$$C_1 = \frac{-1 - D_2 + \frac{\alpha}{K_1 K_2 D_1}}{D_1 - D_2} \quad C_2 = \frac{1 + D_1 - \frac{\alpha}{K_1 K_2 D_2}}{D_1 - D_2}$$

$K_1$=0.466 and $K_2$=1/$K_1$=$\alpha$=2.147.
Using the above equations, the remaining constants can now be calculated.
$E_1$=6.29, $E_2$=5.29
$D_1$=−1.00, $D_2$=−5.29
$C_1$=0.500, $C_2$=0.094
$D_2 k_1$=−1/t2=−0.1199, $k_1$=0.0003778 s$^{-1}$
$K^{\neq}_{anti \to syn}$=$k_1 h/k_b T$=5.18×10$^{-17}$
$\Delta G^{\neq}_{anti \to syn}$=−RT ln $K^{\neq}_{anti \to syn}$=109.2 kJ·mol$^{-1}$.
Also, $D_1 k_1$=−1/t1=−0.01293, $k_1$=0.0002157 s$^{-1}$
$K^{\neq}_{anti \to syn}$=$k_1 h/k_b T$=2.95×10$^{-17}$
$\Delta G^{\neq}_{anti \to syn}$=−RT ln $K^{\neq}_{anti \to syn}$=110.8 kJ·mol$^{-1}$.
Averaging of these two values gives $\Delta G^{\neq}_{anti \to syn}$=110.0 kJ·mol$^{-1}$.
Since $k_2$=$k_1/K_1$, $k_2$=0.0006373 s$^{-1}$
$K^{\neq}_{syn \to anti}$=$k_2 h/k_b T$=8.73×10$^{-17}$
$\Delta G^{\neq}_{syn \to anti}$=−RT ln $K^{\neq}_{syn \to anti}$=107.7 kJ·mol$^{-1}$.

4. Crystallization and X-Ray Diffraction

Figure 18:
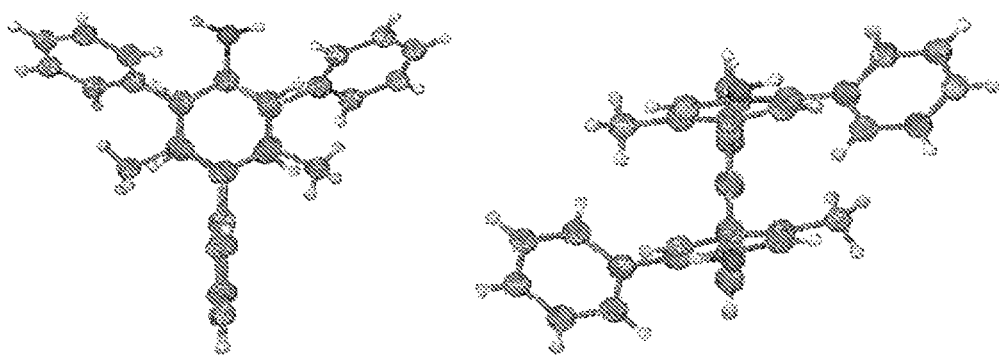
FIG. 18 depicts the single crystal structure of anti-2.

Having determined the stability of 2 to rotation about the chiral axes at room temperature, we decided to investigate the three-dimensional structure of this atropisomer. A single crystal of anti-2 was obtained by slow evaporation of a dichloromethane solution. Crystallographic analysis revealed that the two cofacial phenol rings are almost perfectly aligned due to a torsion angle of only 0.28°. The separation between the centroids of the two phenol rings, which are splayed by 19.48°, was determined as 3.5 Å, indicating substantial x-overlap (FIG. 18).

Single crystal X-ray analysis was performed at 100 K using a Siemens platform diffractometer with graphite monochromated Mo—K$\alpha$ radiation ($\lambda$=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameters.

Figure 19:
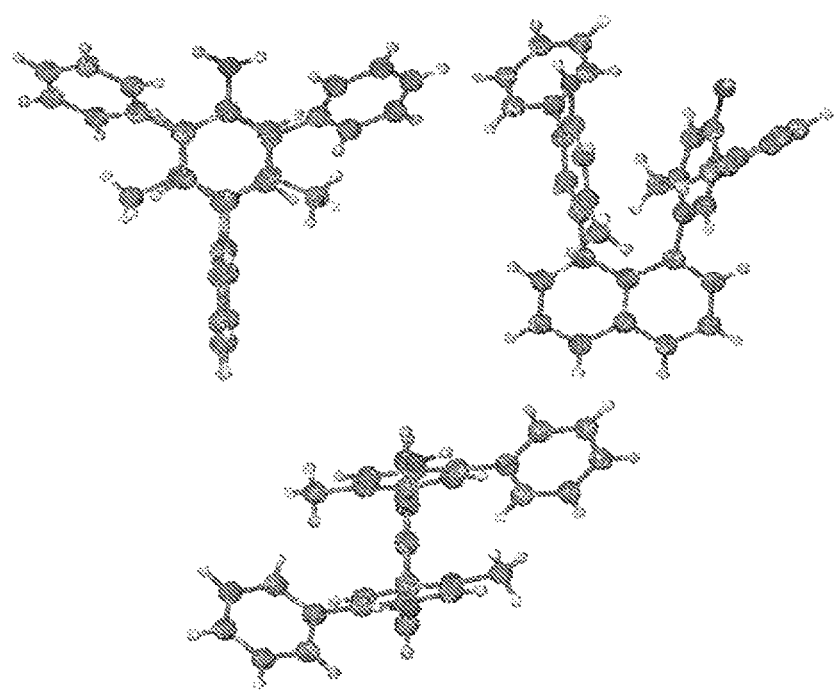
FIG. 19 depicts different views of the crystal structure of 2.

A crystal of 2 was obtained by slow evaporation of a solution of 10.0 mg of 2 in 5 mL of CH$_2$Cl$_2$. Crystal structure data for 2: Formula C$_{36}$H$_{28}$O$_2$, M=492.61, crystal dimensions 0.15×0.15×0.15 mm, monoclinic, space group P21/c, a=11.3010 (23) Å, b=11.8081 (24) Å, c=19.1846 (40) Å, $\beta$=96.897 (3), V=2541.53 Å$^3$, Z=4, $\rho_{calcd}$=1.2872 g cm$^{-1}$. (see FIG. 19)

| | |
|---|---|
| Phenyl-phenyl [Å] (entroids to entroids) | 3.498 |
| Splaying angle between peri-aryl planes [°] | 19.48 |
| Torsion angle [°] | 0.28 |

5. Enantioselective Recognition

Figure 20:
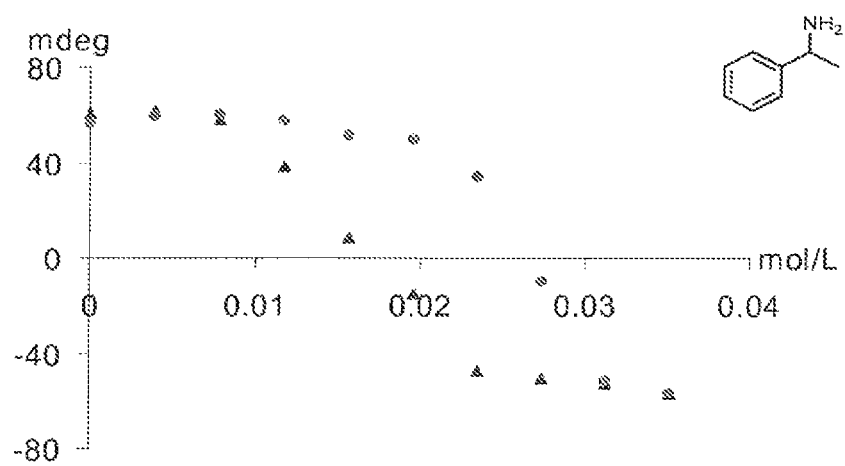
FIG. 20 depicts a change in the CD spectrum of the bisphenoxides of (−)-2 upon addition of (R)-1-phenylethylamine (blue) and the (S)-enantiomer (red). The concentration of 2 was $9.45 \times 10^{-5}$ M in acetonitrile.
Figure 21:
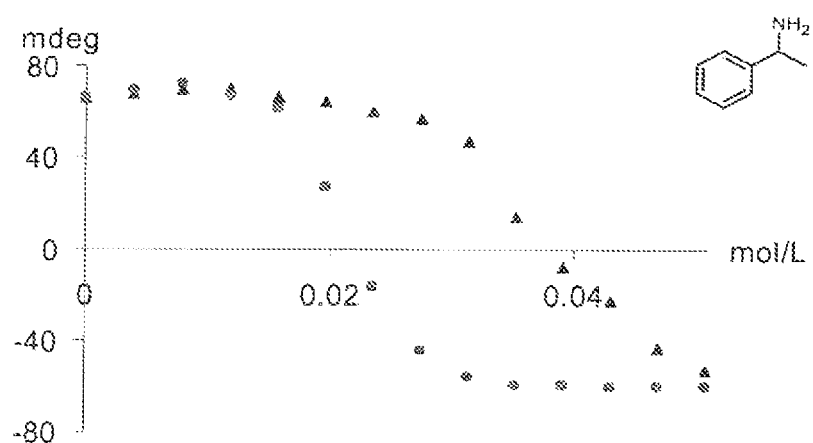
FIG. 21 depicts a change in the CD spectrum of the bisphenoxides of (+)-2 (right) upon addition of (R)-1-phenylethylamine (blue) and the (S)-enantiomer (red). The concentration of 2 was $9.45 \times 10^{-5}$ M in acetonitrile.
Figure 22:
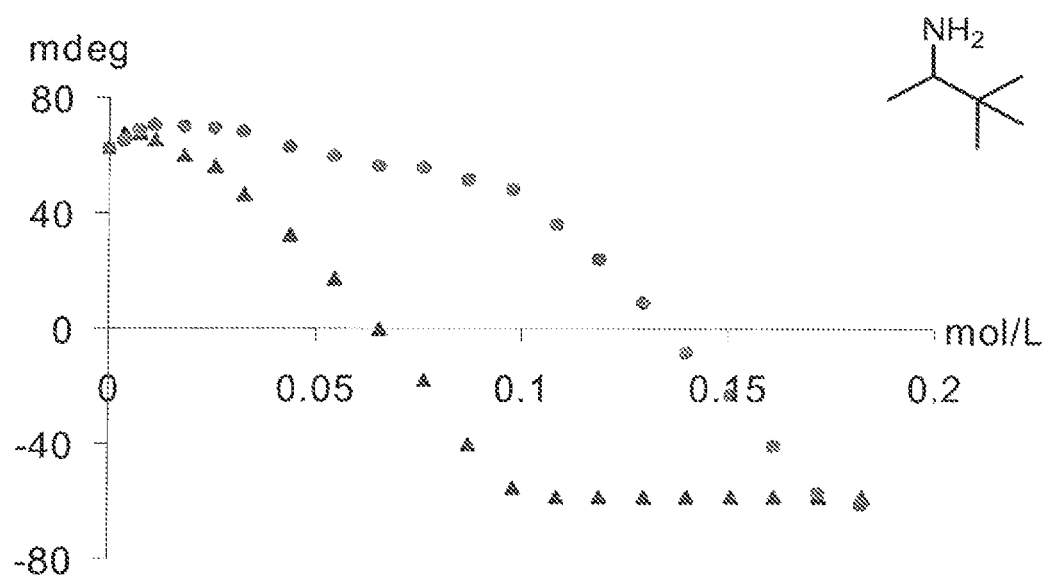
FIG. 22 depicts a change in the CD spectrum of the bisphenoxides of (−)-2 upon addition of (R)-3,3-dimethylbutan-2-amine (blue) and the (S)-enantiomer (red). The concentration of 2 was $9.45 \times 10^{-5}$ M in acetonitrile.
Figure 23:
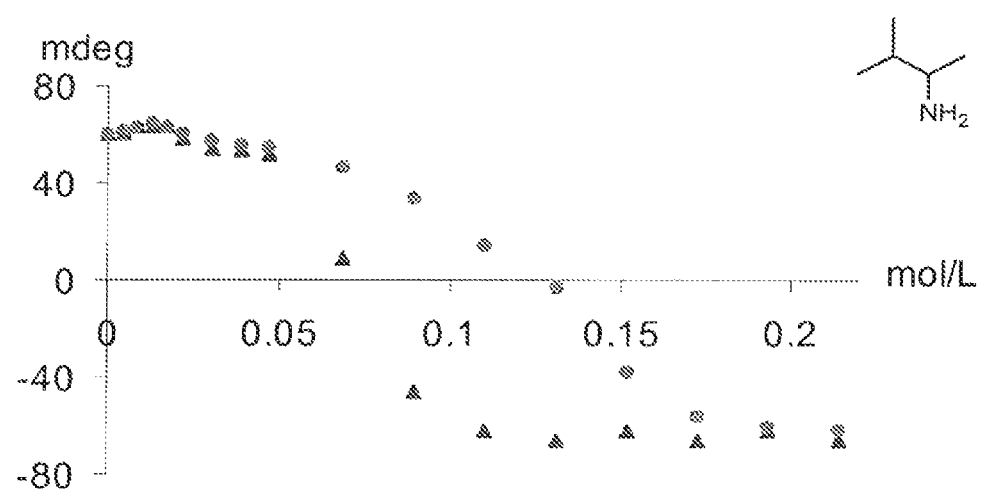
FIG. 23 depicts a change in the CD spectrum of the bisphenoxides of (−)-2 upon addition of (R)-3-dimethylbutan-2-amine (blue) and the (S)-enantiomer (red). The concentration of 2 was $9.45 \times 10^{-5}$ M in acetonitrile.
Figure 24:
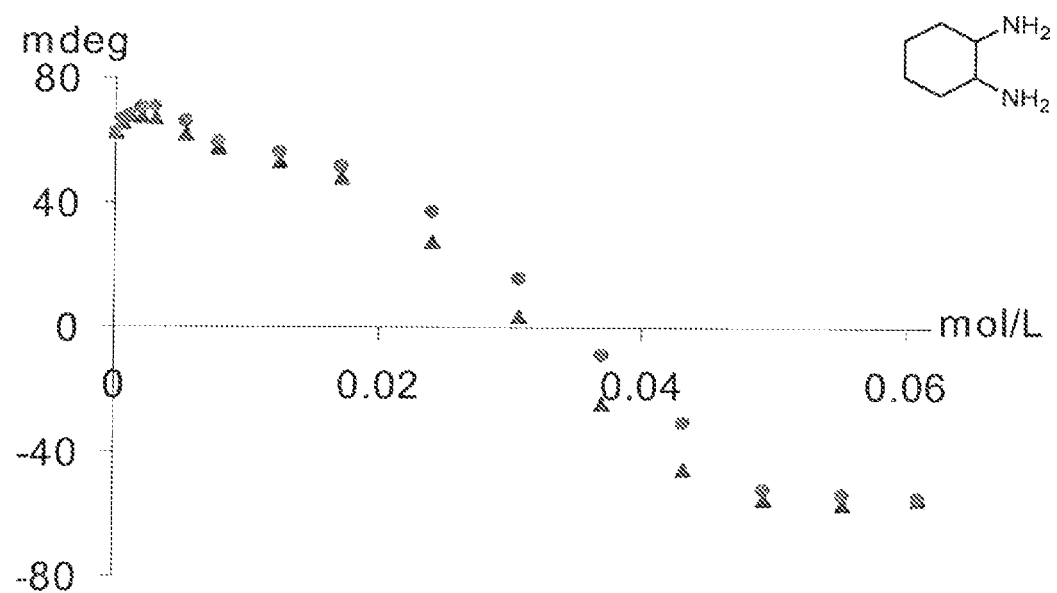
FIG. 24 depicts a change in the CD spectrum of the bisphenoxides of (−)-2 upon addition of (R,R)-cyclohexane-1,2-diamine (blue) and the (S,S)-enantiomer (red). The concentration of 2 was $9.45 \times 10^{-5}$ M in acetonitrile.
Figure 25:
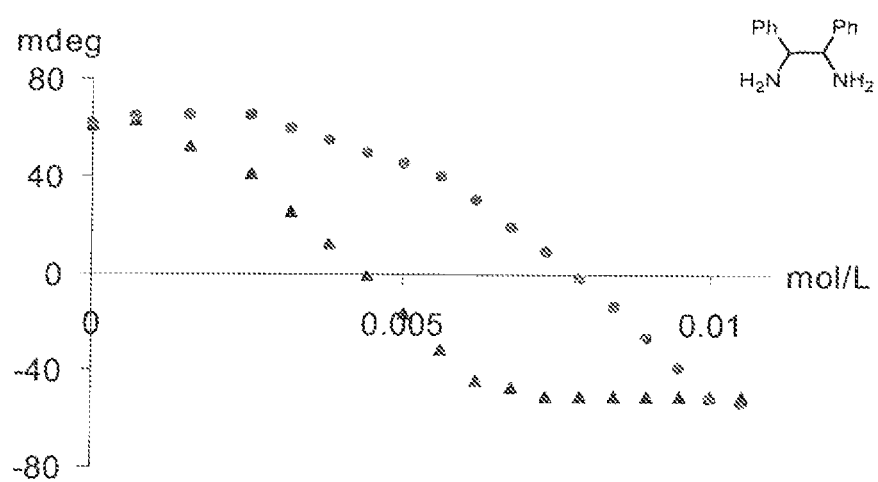
FIG. 25 depicts a change in the CD spectrum of the bisphenoxides of (−)-2 upon addition of (R,R)-1,2-diphenylethane-1,2-diamine (blue) and the (S,S)-enantiomer (red). The concentration of 2 was $9.45 \times 10^{-5}$ M in acetonitrile.
Figure 26:
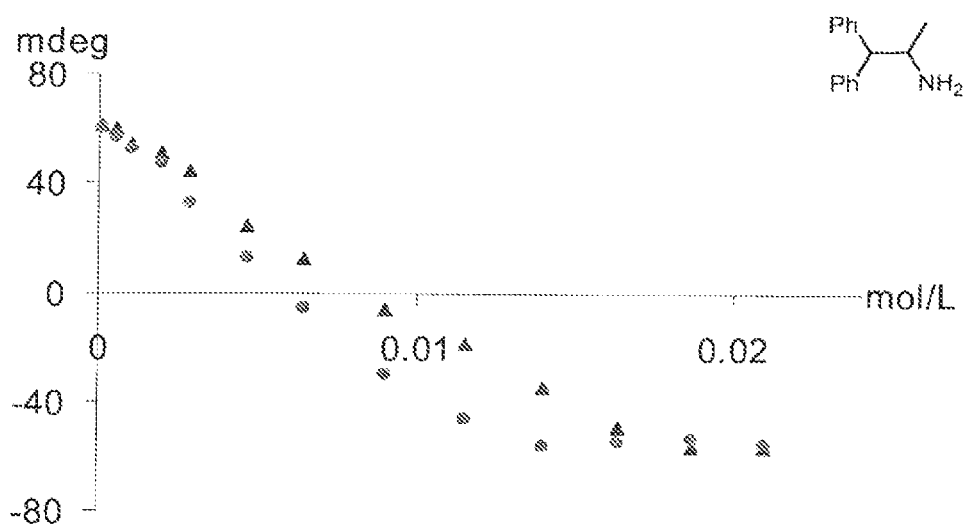
FIG. 26 depicts a change in the CD spectrum of the bisphenoxides of (−)-2 upon addition of (R)-1,1-diphenylpropan-2-amine (blue) and the (S)-enantiomer (red). The concentration of 2 was $9.45 \times 10^{-5}$ M in acetonitrile.
Figure 27:
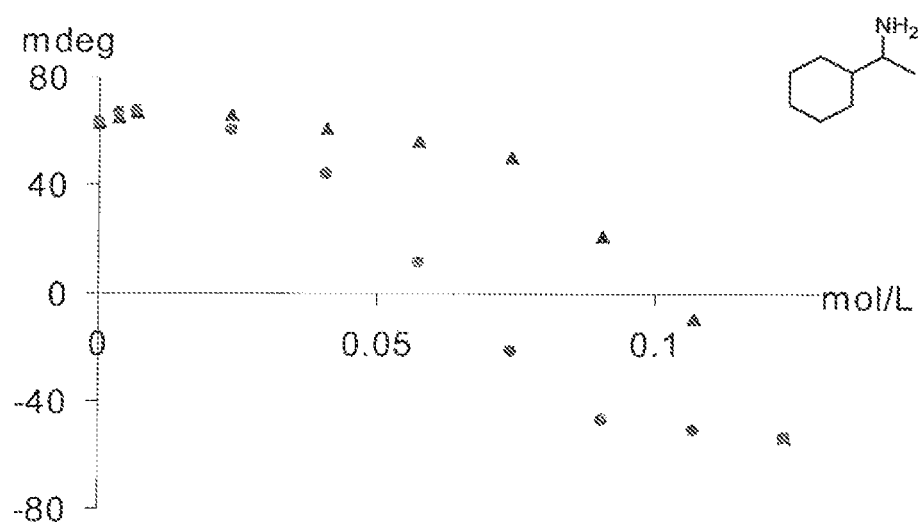
FIG. 27 depicts a change in the CD spectrum of the bisphenoxides of (−)-2 upon addition of (R)-1-cyclohexylethanamine (blue) and the (S)-enantiomer (red). The concentration of 2 was $9.45 \times 10^{-5}$ M in acetonitrile.
Figure 28:
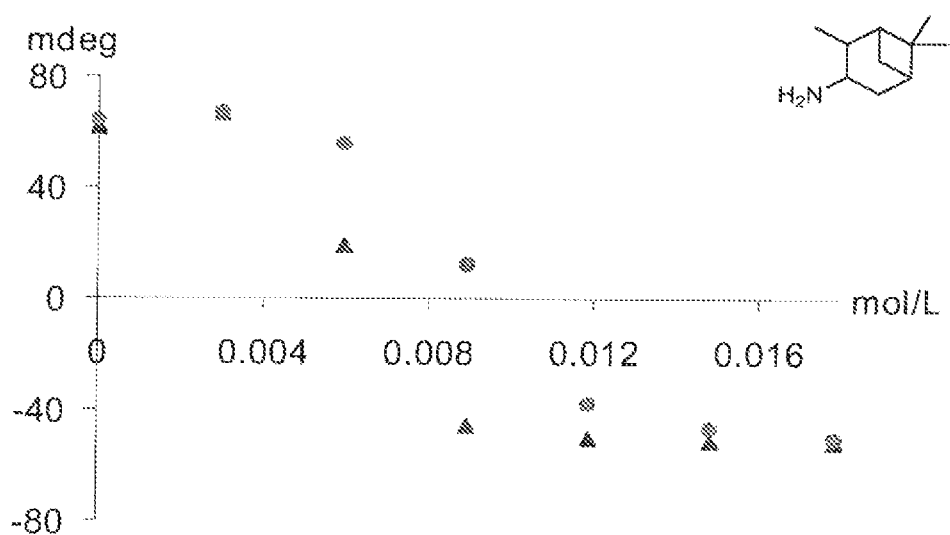
FIG. 28 depicts a change in the CD spectrum of the bisphenoxides of (−)-2 upon addition of (R,R,R,S)-2,6,6-trimethylbicyclo[3.1.1]heptan-3-amine (blue) and the (S,S,S,R)-enantiomer (red). The concentration of 2 was $9.45 \times 10^{-5}$ M in acetonitrile.
Figure 29:
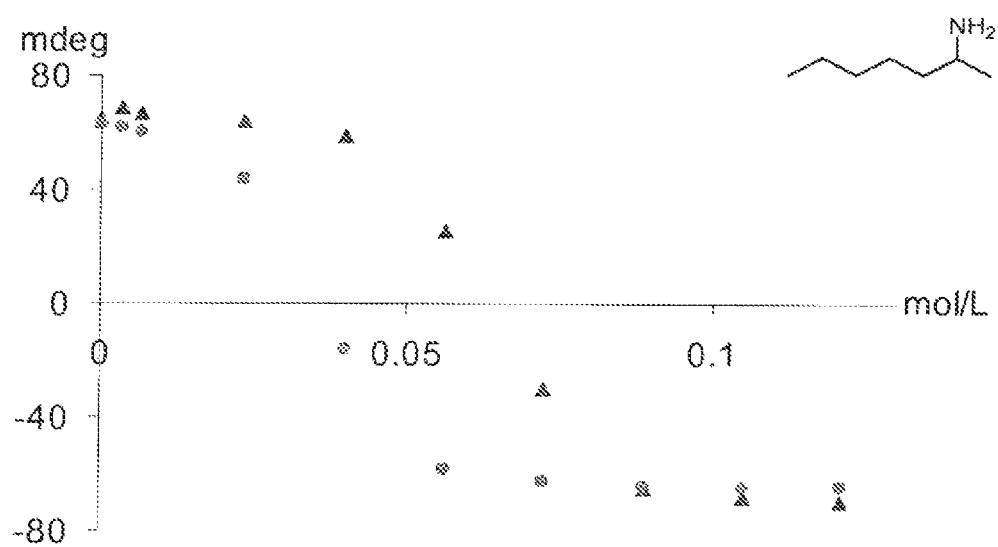
FIG. 29 depicts a change in the CD spectrum of the bisphenoxides of (−)-2 upon addition of (R)-heptan-2-amine (blue) and the (S)-enantiomer (red). The concentration of 2 was $9.45 \times 10^{-5}$ M in acetonitrile.
Figure 30:
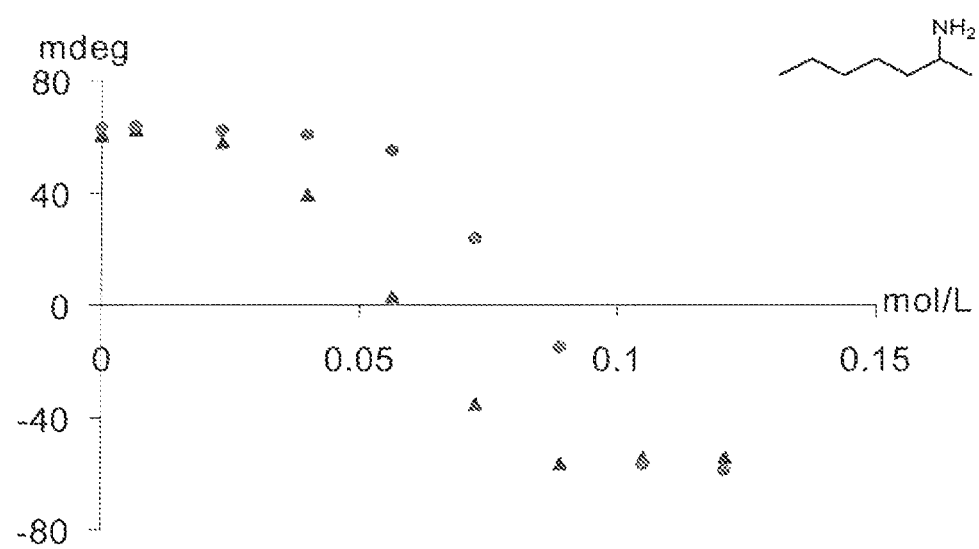
FIG. 30 depicts a change in the CD spectrum of the bisphenoxides of (+)-2 (right) upon addition of (R)-heptan-2-amine (blue) and the (S)-enantiomer (red). The concentration of 2 was $9.45 \times 10^{-5}$ M in acetonitrile.

We now have found that 2 can be used for enantioselective recognition of a wide range of amines. The CD spectra of the enantiomers of 2 are shown in FIG. 15. Upon addition of a sufficiently strong base, the corresponding bisphenolate having a remarkably different CD spectrum is formed. Addition of enantiomers of chiral amines then regenerates the original CD spectrum. This proceeds with high stereoselectivity and therefore allows enantioselective CD sensing of the amine used. Proof-of-concept data were obtained with different analytes, including 1-phenylethylamine, FIG. 20 (shows titration curve with (−)-2); FIG. 21 (shows titration curve with (+)-2). (For CD analysis of amines with chiral metal complexes, see: (a) Nieto, S.; Lynch, V. M.; Anslyn, E. V.; Kim, H.; Chin, J. Org. Lett. 2008, 10, 5167. (b) Nieto, S.; Lynch, V. M.; Anslyn, E. V.; Kim, H.; Chin, J. J. Am. Chem. Soc. 2008, 130, 9232. (c) Nieto, S.; Dragna, J. M.; Anslyn, E. V. Chem. Eur. J. 2010, 16, 227.)

The following conditions have been optimized in terms of reaction time, solvent, concentration and equivalents. Prior to each use, the CD instrument was purged with nitrogen for 20 minutes. Spectra were collected between 240 and 600 nm with a standard sensitivity of 100 mdeg, a data pitch of 0.5 nm, a band width of 0.5 nm, a scanning speed of 1000 nm s$^{-1}$ and a response of 0.5 s using a quartz cuvette (1 cm path length). The concentration of (−)-2 was 9.45×10$^{-5}$ M in ACN. To 2000 μL of (−)-2, 4 equivalents of Na$^t$BuO (0.521 M in DMSO) were added to generate the bisphenoxide of (−)-2, which was titrated with several amine substrates until the original bisphenol CD spectrum was recovered. Ellipticities at 290 nm are then plotted against the concentration of added amine enantiomers. Data obtained with (R)-enantiomers are represented by blue triangles and those obtained with (S)-enantiomer are shown in red (see FIGS. 22-30)

In conclusion, chiral bisphenol 2 has been prepared and used for enantioselective sensing of a wide range of amines.

This study shows the potential of this class of compounds for chiral recognition and it points to the use in asymmetric catalysis.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. An atropisomeric 1,8-bisphenolnaphthalene compound of formula (I):

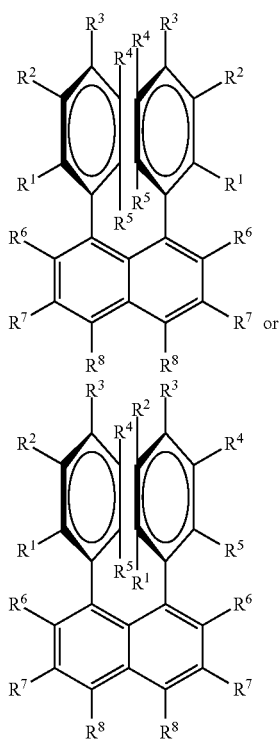

wherein
(a) $R^1$ and $R^5$ are independently selected from the group consisting of hydrogen, alkyl, alkenyl, alkynyl, cycloalkyl, aryl, benzyl, heterocyclyl, heteroaryl, chloro, bromo, iodo, acyl, amino, amido, azido, cyano, formyl, carbamoyl, —$SF_5$, nitro, —OR', —NR"R'", —SR"", $P(O)(OR^A)_2$, —$P(OR^A)_2$, and $P(R^B)_2$, wherein
R' is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical, $P(O)(OR^A)_2$, —$P(OR^A)_2$, and $P(R^B)_2$; or OR' is an optionally substituted saturated or unsaturated, nonaromatic or aromatic heterocyclic radical;
R" and R'" are each independently of one another H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or NR"R'" is an optionally substituted saturated or unsaturated, nonaromatic or aromatic heterocyclic radical;
R"" is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or SR"" is an optionally saturated or unsaturated, nonaromatic or aromatic heterocyclic radical;
$R^A$ is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;
$R^B$ is H, halogen, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;
wherein at least one of $R^1$ and $R^5$ on each phenyl ring is not hydrogen;
(b) $R^2$, $R^4$, $R^6$, $R^7$ and $R^8$ are independently selected from the group consisting of hydrogen, alkyl, alkenyl, alkynyl, cycloalkyl, aryl, benzyl, heteroalkyl, heterocyclyl, heterocycloalkyl, heteroaryl, halogen, acyl, amino, amido, azido, alkyliminyl (—C=NH-alkyl), carboxy, cyano, formyl, carbamoyl, —$SF_5$, nitro, OR', NR"R'", SR"", $P(O)(OR^A)_2$, —$P(OR^A)_2$, and $P(R^B)_2$,
$R^3$ is selected from the group consisting of hydrogen, alkyl, alkenyl, alkynyl, cycloalkyl, unsubstituted aryl, benzyl, heteroalkyl, unsubstituted heterocyclyl, heteroaryl, halogen, acyl, amino, amido, azido, alkyliminyl (—C=NH-alkyl), carboxy, cyano, formyl, carbamoyl, —$SF_5$, nitro, OR', NR"R'", SR"", $P(O)(OR^A)_2$, —$P(OR^A)_2$, and $P(R^B)_2$, wherein
R' is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical, $P(O)(OR^A)_2$, —$P(OR^A)_2$, and $P(R^B)_2$; or OR' is an optionally substituted saturated or unsaturated, nonaromatic or aromatic heterocyclic radical;
R" and R'" are each independently of one another H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or NR"R'" is an optionally substituted saturated or unsaturated, nonaromatic or aromatic heterocyclic radical;
R"" is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical; or SR"" is an optionally saturated or unsaturated, nonaromatic or aromatic heterocyclic radical;
$R^A$ is H, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;
$R^B$ is H, halogen, alkyl, alkenyl, alkynyl, cycloalkyl, cycloalkenyl, an (acyclic or cyclic) hydrocarbon radical, hydrocarbonoxy radical, a heterocyclyl radical, heterocyclyloxy radical, heterocyclylthio radical or heterocyclylamino radical;
wherein at least one of $R^2$ and $R^4$ on each phenyl ring is not hydrogen.

2. An atropisomeric 1,8-bisphenolnaphthalene of claim 1, wherein
   (a) $R^1$ and $R^5$ are independently selected from the group consisting of hydrogen, ($C_1$-$C_4$) alkyl, phenyl, chloro, bromo and iodo, wherein at least one of $R^1$ and $R^5$ on each phenyl ring is not hydrogen;
   (b) $R^2$ and $R^4$ are independently selected from the group consisting of hydrogen, ($C_1$-$C_4$) alkyl, ($C_2$-$C_4$) alkenyl, ($C_2$-$C_4$) alkynyl, ($C_3$-$C_6$) cycloalkyl, phenyl, ($C_1$-$C_6$) acyl, and formyl, wherein at least one of $R^2$ and $R^4$ on each phenyl ring is not hydrogen;
   (c) $R^3$ is independently $PR'_2$, $NR'_2$ or $OR'$ wherein each R' is independently H or ($C_1$-$C_4$) alkyl, and
   (d) $R^6$, $R^7$ and $R^8$ are independently selected from the group consisting of hydrogen, ($C_1$-$C_4$) alkyl, hydroxyl, ($C_1$-$C_4$) alkoxy, halogen, $NH_2$, amido, azido, cyano, formyl, carbamoyl, nitro.

3. An atropisomeric 1,8-bisphenolnaphthalene of claim 2, wherein
   (a) $R^1$ and $R^5$ are independently H and methyl, wherein at least one of $R^1$ and $R^5$ on each phenyl ring is not hydrogen;
   (b) $R^2$ and $R^4$ are independently phenyl or formyl, wherein at least one of $R^2$ and $R^4$ on each phenyl ring is not hydrogen;
   (c) $R^3$ is independently OR' wherein R' is H or methyl; and
   (d) $R^6$, $R^7$ and $R^8$ are independently selected from the group consisting of hydrogen and methyl.

4. An atropisomeric 1,8-bisphenolnaphthalene compound of claim 3, wherein compound has the structure of formula 5 below:

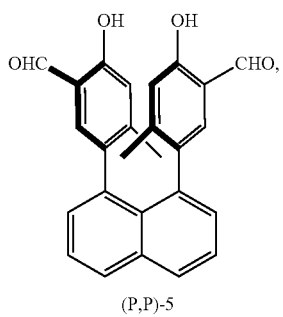

(P,P)-5 or
   its enantiomer.

5. An atropisomeric 1,8-bisphenolnaphthalene compound of claim 3, wherein compound has the structure of formula 2 below:

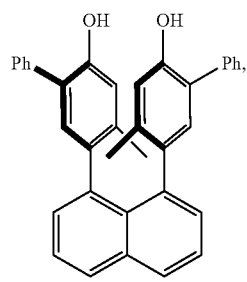

(2)

or
   its enantiomer.

6. An atropisomeric 1,8-bisphenolnaphthalene compound of compound of claim 1 where in the compound is stable to racemization at room temperature (20-25° C.).

7. A method of providing enantiomeric recognition between stereoisomers of a chiral compound, which comprises of adding an atropisomeric 1,8-bisphenolnaphthalene compound of claim 1 to a solution containing a racemic or diasteriomeric mixture of the chiral compound, wherein the chiral compound is an amine, amino alcohol amino acid or alcohol.

8. The method of claim 7, wherein the atropisomeric 1,8-bisphenolnaphthalene compound has the structure of formula 2 below:

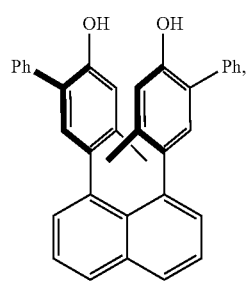

(2)

or
   its enantiomer.

9. The method of claim 7, wherein the chiral amine is selected from the group consisting of 1-phenylethylamine, 3,3-dimethylbutan-2-amine, 3-dimethylbutan-2-amine, cyclohexane-1,2-diamine, 1,2-diphenylethane-1,2-diamine, 1,1-diphenylpropan-2-amine, 1-cyclohexylethanamine, 2,6,6-trimethylbicyclo[3.1.1]heptan-3-amine, and heptan-2-amine.

* * * * *